United States Patent [19]
Isobe et al.

[11] Patent Number: 5,661,153
[45] Date of Patent: Aug. 26, 1997

[54] 1-ARYLPYRIMIDINE DERIVATIVES AND PHARMACEUTICAL USE THEREOF

[75] Inventors: Yoshiaki Isobe, Toda; Toshimasa Katagiri, Okayama; Junko Umezawa, Toda; Yuso Goto, Toda; Masashi Sasaki, Toda; Nobuo Watanabe, Toda; Hideharu Sato, Toda; Fumihiro Obara, Toda, all of Japan

[73] Assignee: Japan Energy Corporation, Tokyo, Japan

[21] Appl. No.: 463,277

[22] Filed: Jun. 5, 1995

[30] Foreign Application Priority Data

Jul. 19, 1994 [JP] Japan .................................. 6-167222
Aug. 18, 1994 [JP] Japan .................................. 6-194219

[51] Int. Cl.$^6$ .................................................. A61K 31/52
[52] U.S. Cl. .......................... 514/261; 514/262; 514/269; 514/274; 544/267; 544/311
[58] Field of Search .................................. 544/311, 267; 514/261, 262, 269, 274

[56] References Cited

U.S. PATENT DOCUMENTS

| | | | |
|---|---|---|---|
| 4,452,788 | 6/1984 | Bristol et al. | 544/267 |
| 4,548,820 | 10/1985 | Regnier et al. | 514/255 |

FOREIGN PATENT DOCUMENTS

| | | | |
|---|---|---|---|
| 0001735 | 2/1979 | European Pat. Off. . | |
| 0 001735 | 5/1979 | European Pat. Off. . | |
| 0 435811 | 7/1991 | European Pat. Off. . | |
| 9109859 | 7/1991 | WIPO | 544/267 |
| WO91/17993 | 11/1991 | WIPO . | |
| WO91/19717 | 12/1991 | WIPO . | |
| WO92/05176 | 4/1992 | WIPO . | |

OTHER PUBLICATIONS

Patent Abstracts of Japan, JP-3-204880, Sep. 6, 1991.
Patent Abstracts of Japan, JP-3-264585, Nov. 25, 1991.
Patent Abstracts of Japan, JP-5-194515, Aug. 3, 1993.
English Abstract of WO 93/12120, Jun. 24, 1993.
English Abstract of WO 93/12116, Jun. 24, 1993.
English Abstract of WO 93/11127, Jun. 10, 1993.
Patent Abstracts of Japan, JP-3-128375, May 31, 1991.
Patent Abstracts of Japan, JP-3-173888, Jul. 29, 1991.
Patent Abstracts of Japan, JP-3-204879, Sep. 6, 1991.
Allergy, vol. 41, No. 8, pp. 594–602, 1986, M. Dahlbaeck, et al., "Antigen–Induced Bronchial Anaphylaxis in Actively Sensitized SD Rats".
Chemische Berichte, vol. 111, No. 3, pp. 982–995, 1978, H. Fuchs, et al., "Ueber Die Cyclisierung Von 4–Alkylamino–5–Nitrosouracacilen Und Die Synthese Von 8–Substituierten Xanthinen Und Bis(Theophyllin–8–yl)–Alkan–Derivaten".
Chemical Abstracts, vol. 87, No. 15, Oct. 10, 1977, AN–117907p, p. 605.
Chemical Abstracts, vol. 88, No. 7, Feb. 13, 1978, AN–50930r, p. 556.
Chemical Abstracts, vol. 121, No. 23, Dec. 5, 1994, AN–280660g, p. 1037.

*Primary Examiner*—Matthew V. Grumbling
*Assistant Examiner*—Michael Bucknum
*Attorney, Agent, or Firm*—Oblon, Spivak, McClelland, Maier & Neustadt, P.C.

[57] ABSTRACT

The present invention relates to 1-arylpyrimidine derivatives represented by general formula (I):

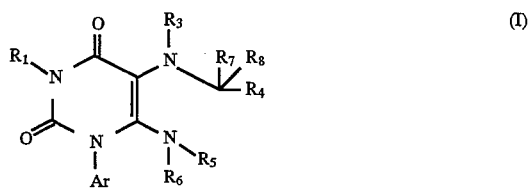

wherein
$R_1$ is H, alkyl or aralkyl;
Ar is 1-naphthyl, or a substituted or unsubstituted phenyl group;
$R_4$ is a substituted phenyl, a substituted styryl, 1-methylcyclohexyl, 4-methylcyclohexyl, 4-oxo-4H-pyran-2-yl or 2-oxo-2H-pyran-5-yl group;
$R_5$ and $R_6$ are each independently H or alkyl;
$R_3$ is H, and $R_7$ and $R_8$ are combined together to be oxo, or else $R_3$ and $R_7$ are combined together to be another direct bond, and $R_5$ and $R_8$ are combined together to be a direct bond,
or pharmaceutically acceptable salts thereof; and methods for treating allergic diseases with such compounds.

31 Claims, No Drawings

1-ARYLPYRIMIDINE DERIVATIVES AND PHARMACEUTICAL USE THEREOF

BACKGROUND OF THE INVENTION

1. Field of the Invention

The present invention relates to novel pyrimidine derivatives having an aryl group at the 1-position and methods for treating allergic disorders therewith, particularly, methods for treating inflammatory allergic disorders such as asthma, dermatitis, rhinitis and the like, or graft-versus-host disease (GVHD) which occurs at organ transplantation.

2. Description of the Prior Art

Allergy is classified in four types I to IV. It is believed that so-called allergic disorders are mainly due to types I and IV. Atopic dermatitis has heretofore been believed to be an allergic disorder that is mainly due to type I allergy. However, in recent studies, it has been reported that atopic dermatitis is a disorder that is due to allergies of both types I and IV and in which the contribution of type IV is greater than that of type I. Type I allergy is called humoral immunity whereas type IV allergy is called cellular immunity. The mechanism of action is very different in the two types (Protein.Nucleic Acid.Enzyme, 36, 839–847 (1991)). In particular, there is a large difference in T cells that partake in their immunological mechanisms. $Th_2$ cells play an important role in the type I allergy whereas $Th_1$ cells do in the type IV allergy (J. Immunology, 138, 3688–3694 (1987)). In fact, commercially available therapeutic agents for type I allergy (e.g., anti-histamines, etc.) are not very effective against atopic dermatitis in clinical practice whereas steroid agents that exhibit effect on allergies of both types I and IV are clinically effective. Furthermore, it can be understood from the clinical effect of immunosuppresive agents (e.g., cyclosporine, FK-506, etc.) which are type IV allergy-inhibiting agents that type IV allergy is the main cause of atopic dermatitis. In other allergic disorders, for example, asthma, the cause of its initial onset is type I allergy but the subsequently occurring inflammation of the airway which may cause chronicity or incurability of asthma is due to type IV allergy (Allergy, 37, 12–18 (1988)). In addition, it has been experimentally found that type IV allergy can induce asthma and it has been reported that cyclosporine and the like are effective in the treatment of asthma (Amer. Rev. Resir. Dis., 144, 931–938 (1991); Allergy, 39, 482–487 (1990); and Allergy, 39, 605–609 (1990)). In the treatment of asthma, anti-type I allergic agents such as anti-histamines are administered only supplementally in mild cases and steroid agents are mainly used in the present situation.

For the aforementioned reasons, steroid agents that are effective against allergies of both types I and IV are administered in combination in the case of allergic disorders of a mixed type or those in which the contribution of type IV allergy is predominant. However, as is well known, clinically effective steroid agents cause various side-effects such as infectious diseases, adrenal retraction, osteoporosis, psychiatric disorders, diabetes and the like and are therefore unsuitable for long term or continuous administration. Hence, non-steroid compounds which are effective against both types I and IV can potentially be good therapeutic agents for a wide variety of allergic disorders and their development is desired.

There have been suggested several non-steroid compounds that are effective against allergic disorders. For example, the applicant has already proposed pyrimidine derivatives that are composed of a pyrimidine ring and a phenyl group, wherein the pyrimidine ring is substituted with various hydrocarbon groups at the 3- and 1-positioned nitrogen atoms and the phenyl group has lower alkyl substituents at the 3- and 5-positions and a hydroxy group at the 4-position, as disclosed in Japanese Patent Laid-Open Publication No. 5-194424; and uracil derivatives which are composed of an uracil ring and a phenyl group, wherein the uracil ring is substituted with various hydrocarbon groups at the 3- and 1-positioned nitrogen atoms and the phenyl group has lower alkyl substituents at the 3- and 5-positions and a hydroxy group at the 4-position, as disclosed in Japanese Patent Laid-Open Publication No. 6-135943.

Nevertheless, the development of novel non-steroid compounds having a better effect as therapeutic agents for allergic disorders of I and IV mixed type or those in which the contribution of type IV allergy is predominant is still desired strongly. In particular, there is a great demand for non-steroid compounds that can be administered orally and which are more suitable for long-term or continuous administration in the treatment of chronic allergic disorders such as atopic dermatitis, asthma and the like.

OBJECTS AND SUMMARY OF THE INVENTION

An object of the present invention is to solve the aforementioned problems. In other words, an object of the present invention is to provide novel therapeutic agents for allergy which are effective against allergies of both types I and IV, particularly, to provide non-steroid, low molecular weight compounds that can be administered orally and which are more suitable for long term or continuous administration.

As a result of the various studies conducted to develop novel agents that are effective in treating allergic disorders for the purpose of solving the aforementioned problems, the inventors produced 1-arylpyrimidine derivatives represented by the following general formula (I) and salts thereof, and found that these compounds have not only an excellent effect on type IV allergy but also a remarkable effect on type I-allergy, thereby accomplishing the present invention.

The present invention encompasses the following inventions.

(1) A 1-arylpyrimidine derivative represented by general formula (I):

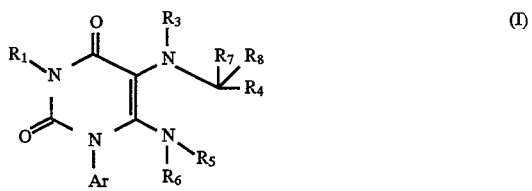

wherein $R_1$ is H, $C_{1-6}$ alkyl or aralkyl;

Ar is 1-naphthyl or a group represented by general formula (II):

wherein $R_2$ is H, halogen, $C_{1-4}$ alkyl or $C_{1-4}$ alkoxy;

$R_4$ is a group represented by general formula (III):

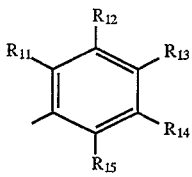

wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, a group represented by general formula (IV):

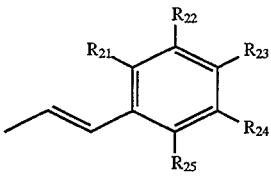

wherein $R_{21}$, $R_{22}$, $R_{23}$, $R_{24}$ and $R_{25}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, 1-methylcyclohexyl, 4-methylcyclohexyl, 4-oxo-4 H-pyran-2-yl or 2-oxo-2H-pyran-5-yl;

$R_5$ and $R_6$ are each independently H or $C_{1-4}$ alkyl;

$R_3$ is H, and $R_7$ and $R_8$ are combined together to be oxo, or else $R_3$ and $R_7$ are combined together to be another direct bond, and $R_5$ and $R_8$ are combined together to be a direct bond, or a pharmaceutically acceptable salt thereof.

(2) The compound of (1), wherein the 1-arylpyrimidine derivative is represented by general formula (Ia):

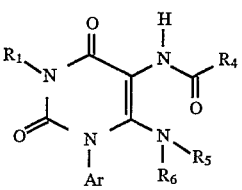

wherein $R_1$, $R_4$ and Ar are as defined above, and $R_5$ and $R_6$ are each independently H or $C_{1-4}$ alkyl.

(3) The compound of (2), wherein $R_5$ or $R_6$ in the general formula (Ia) is H.

(4) The compound of (2) or (3), wherein $R_4$ in the general formula (Ia) is a group represented by the general formula (III).

(5) The compound of any one of (2)–(4), wherein Ar in the general formula (Ia) is a group represented by the general formula (II).

(6) The compound of (2), (3) or (5), wherein $R_4$ in the general formula (Ia) is a group represented by the general formula (IV).

(7) The compound of (2), (3) or (5), wherein $R_4$ in the general formula (Ia) is 1-methylcyclohexyl, 4-methylcyclohexyl, 4-oxo-4H-pyran-2-yl, or 2-oxo-2H-pyran-5-yl.

(8) The compound of any one of (2)–(4), wherein Ar in the general formula (Ia) is 1-naphthyl.

(9) The compound of (2), (3), (4), (5) or (8), wherein $R_4$ in the general formula (Ia) is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

(10) The compound of (6), wherein $R_4$ in the general formula (Ia) is a group represented by the general formula (IV) wherein $R_{21}$, $R_{22}$, $R_{23}$, $R_{24}$ and $R_{25}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

(11) The compound of (3), (4), (8) or (9), wherein Ar in the general formula (Ia) is 1-naphthyl and $R_4$ is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

(12) The compound of (5), wherein Ar in the general formula (Ia) is a group represented by the general formula (II) wherein $R_2$ is a substituent at the p-position.

(13) The compound of (3), (4), (5), (8), (9) or (11), wherein $R_4$ in the general formula (Ia) is a group represented by the general formula (III) wherein $R_{12}$, $R_{13}$ and $R_{14}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{11}$ and $R_{15}$ are H.

(14) The compound of (10), wherein $R_4$ in the general formula (Ia) is a group represented by the general formula (IV) wherein $R_{22}$, $R_{23}$ and $R_{24}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{21}$ and $R_{25}$ are H.

(15) The compound of (13), wherein $R_4$ in the general formula (Ia) is a group represented by the general formula (III) wherein $R_{12}$, $R_{13}$ and $R_{14}$ are each independently H, OH, $C_{2-10}$ alkanoyloxy or $C_{2-10}$ alkoxycarbonyloxy, provided that at least two of them are not H, and both $R_{11}$ and $R_{15}$ are H.

(16) The compound of (15), wherein $R_4$ in the general formula (Ia) is 3,5-diacetoxyphenyl, 3,5-dihydroxyphenyl, 3,4,5-triacetoxyphenyl, 3,4,5-trihydroxyphenyl, 3,4-diacetoxyphenyl or 3,4-dihydroxyphenyl.

(17) The compound of (1), wherein the 1-arylpyrimidine derivative of the general formula (I) is represented by general formula (Ib):

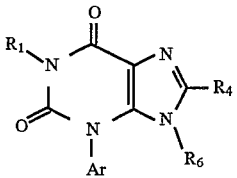

wherein $R_1$ and $R_6$ are as defined above, Ar is a group represented by the general formula (II) and $R_4$ is a group represented by the general formula (III).

(18) The compound of (17), wherein $R_6$ in the general formula (Ib) is H.

(19) The compound of (18), wherein Ar in the general formula (Ib) is a group represented by the general formula (II) wherein $R_2$ is a substituent at the p-position.

(20) The compound of (18) or (19), wherein $R_4$ in the general formula (Ib) is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

(21) The compound of (20), wherein $R_4$ in the general formula (Ib) is a group represented by the general formula (III) wherein $R_{12}$, $R_{13}$ and $R_{14}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{11}$ and $R_{15}$ are H.

(22) The compound of (21), wherein $R_4$ in the general formula (Ib) is a group represented by the general formula (III) wherein $R_{12}$, $R_{13}$ and $R_{14}$ are each independently H, OH, $C_{2-10}$ alkanoyloxy or $C_{2-10}$ alkoxycarbonyloxy, provided that at least two of them are not H, and both $R_{11}$ and $R_{15}$ are H.

(23) The compound of (22), wherein $R_4$ in the general formula (Ib) is 3,5-diacetoxyphenyl, 3,5-dihydroxyphenyl, 3,4,5-triacetoxyphenyl, 3,4,5-trihydroxyphenyl, 3,4-diacetoxyphenyl or 3,4-dihydroxyphenyl.

(24) A method for treating asthma-accompanied bronchoconstriction with the compound of (1).

(25) A method for treating atopic dermatitis with the compound of (1).

(26) A method for treating an allergic disorder with the compound of (1).

(27) A method for treating graft-versus-host disease with the compound of (1).

The specific compounds of the 1-arylpyrimidine derivatives of the present invention are not designated as derivatives having substituents in the 2,4-dioxopyrimidine ring but designated in the following manner. The 1-arylpyrimidine derivatives represented by the general formula (Ia) are designated generally as derivatives having substituents in the uracil ring where their pyrimidine ring are present as 2,4-dioxopyrimidine ring. The 1-arylpyrimidine derivatives represented by the general formula (Ib) are designated generally as derivatives having substituents in the purine ring where their pyrimidine ring (uracil ring) is condensed at the 5- and 6-positions with an imidazole ring to form pyrimido[5,6-d]imidazole. As described below, the 1-arylpyrimidine derivatives represented by the general formula (Ib) correspond to cyclized derivatives that form imidazole ring by ring closure.

In the general formulae, the $C_{1-4}$ alkyl of $R_2$, $R_5$, $R_6$, $R_{11}$, $R_{12}$, $R_{13}$, $R_{14}$, $R_{15}$, $R_{21}$, $R_{22}$, $R_{23}$, $R_{24}$ or $R_{25}$ may be straight or branched. The straight alkyl includes methyl, ethyl, propyl and butyl. The branched alkyl includes isopropyl, isobutyl, sec-butyl and tert-butyl. The $C_{1-4}$ alkoxy of $R_2$, $R_{11}$, $R_{12}$, $R_{13}$, $R_{14}$, $R_{15}$, $R_{21}$, $R_{22}$, $R_{23}$, $R_{24}$ or $R_{25}$ may be one whose alkyl part is straight or branched. The straight alkoxy includes methoxy, ethoxy, propoxy and butoxy. The branched alkoxy includes isopropoxy, isobutoxy, sec-butoxy and tert-butoxy. The $C_{1-6}$ alkyl of $R_1$ may be straight or branched and include the $C_{1-4}$ alkyl mentioned above, pentyl, tert-pentyl, hexyl and the like. The aralkyl (arylalkyl) of $R_1$ includes aralkyl containing a $C_{1-3}$ alkylene chain, for example, benzyl and phenethyl.

In the general formulae, the $C_{2-10}$ alkanoyloxy of $R_{11}$, $R_{12}$, $R_{13}$, $R_{14}$, $R_{15}$, $R_{21}$, $R_{22}$, $R_{23}$, $R_{24}$ or $R_{25}$ may be one whose alkyl part is straight or branched. The straight alkanoyloxy includes acetoxy(ethanoyloxy), propionyloxy (propanoyloxy), butyryloxy(butanoyloxy), valeryloxy (pentanoyloxy) and the like. The branched alkanoyloxy includes isobutyryloxy(2-methylpropanoyloxy), isovaleryloxy(3-methylbutanoyloxy), pivaloyloxy(2,2-dimethylpropanoyloxy) and the like. The $C_{2-10}$ alkoxycarbonyloxy of $R_{11}$, $R_{12}$, $R_{13}$, $R_{14}$, $R_{15}$, $R_{21}$, $R_{22}$, $R_{23}$, $R_{24}$ or $R_{25}$ may be one whose alkyl part is straight or branched. The straight alkoxycarbonyloxy includes methoxycarbonyloxy, ethoxycarbonyloxy, propoxycarbonyloxy and the like. The branched alkoxycarbonyloxy includes isopropoxycarbonyloxy, isobutoxycarbonyloxy, sec-butoxycarbonyloxy, tert-butoxycarbonyloxy and the like.

In the general formula (I), the substituent $R_1$ includes generally $C_{1-6}$ aklyl and aralkyl containing a $C_{1-3}$ alkylene chain. The $C_{1-4}$ alkyl mentioned above and benzyl that is aralkyl(arylalkyl) containing a methylene group are preferred and straight alkyl, particularly methyl, is more preferred as the alkyl.

In the general formula (Ia), the amino group which is a substituent on the carbon atom at the 6-position of the uracil ring includes amino (both $R_5$ and $R_6$ are H); monosubstituted amino (either $R_5$ or $R_6$ is H and the other is the $C_{1-4}$ alkyl mentioned above), for example, methylamino, ethylamino, propylamino and butylamino; di-substituted amino (both $R_5$ and $R_6$ are the $C_{1-4}$ alkyl mentioned above), for example, dimethylamino.

In the general formula (Ib), the substituent $R_6$ on the nitrogen atom at the 9-position of the purine ring includes H and the $C_{1-4}$ alkyl mentioned above.

In the general formula (Ia), Ar includes substituted or unsubstituted phenyl group represented by the general formula (II) and 1-naphthyl group. In the general formula (II), $R_2$ includes the $C_{1-4}$ alkyl and $C_{1-4}$ alkoxyl mentioned above and halogen. The halogen means fluorine, chlorine, bromine, or iodine atom and preferred are fluorine and chlorine atoms. As the $C_{1-4}$ alkyl, straight alkyl is preferred and methyl is more preferred. As the $C_{1-4}$ alkoxyl, those comprising a straight alkyl group are preferred and methoxy is more preferred.

Ar includes those in which the substituent $R_2$ is substituted at any position on the phenyl group, that is, at the o-, m- or p-position. Preferred examples of the substituted phenyl group as Ar include 4-fluorophenyl, 2-fluorophenyl, 4-methylphenyl, 4-methoxyphenyl, 4-chlorophenyl, 2-chlorophenyl, 3-fluorophenyl, 3-chlorophenyl and the like. In general, those in which the substituent $R_2$ is substituted at the p-position are preferred and particularly, phenyl groups in which preferable halogen, methyl or methoxy is substituted at the p-position as the substituent $R_2$ are more preferred.

In the general formula (Ib), 1-naphthyl can be selected as Ar but this group frequently causes steric hindrance with the substituent $R_6$ on the nitrogen atom at the 9-position of the purine ring. The selection of a substituted or an unsubstituted phenyl group represented by the general formula (II)is preferred since they avoid the above disadvantage. The substituent $R_2$ in the general formula (II) includes the $C_{1-4}$ alkyl and $C_{1-4}$ alkoxyl mentioned above and halogen. The halogen means fluorine, chlorine, bromine, or iodine atom and fluorine and chlorine atoms are preferred. As the $C_{1-4}$ alkyl, straight alkyl groups are preferred and methyl group is more preferred. As the $C_{1-4}$ alkoxyl, those comprising a straight alkyl group are preferred and methoxy is more preferred. In particular, phenyl groups in which preferable halogen, methyl or methoxy is substituted at the p-position as the substituent $R_2$ are more preferred as in the case of the general formula (Ia).

In the general formula (Ia), an atomic group represented by $R_4$ is preferably a group represented by the general formula (III). Preferred are those in which at least one of the substituents $R_{11}$, $R_{12}$, $R_{13}$, $R_{14}$ and $R_{15}$ in the general formula (III) is OH, $C_{2-10}$ alkanoyloxy, $C_{2-10}$ alkoxycarbonyloxy or $C_{1-4}$ alkoxy, for example, 3,5-dimethoxyphenyl. More preferred are those in which the above-mentioned substituents are selected from among OH, $C_{2-10}$ alkanoyloxy and $C_{2-10}$ alkoxycarbonyloxy. Specific examples include 4-acetoxyphenyl, 2-acetoxyphenyl, 3-acetoxyphenyl, 4-hydroxyphenyl, 2-hydroxyphenyl, 3-hydroxyphenyl, 3,4-diacetoxyphenyl, 3,4-dihydroxyphenyl, 3,5- diacetoxyphenyl, 3,5-dihydroxyphenyl, 3,4,5-triacetoxyphenyl, 3,4,5-trihydroxyphenyl, 2,3-diacetoxyphenyl, 2,3-dihydroxyphenyl, 3,5-diacetoxy-4-methylphenyl and the like.

More preferred are those in which at least two of the substituents $R_{11}$, $R_{12}$, $R_{13}$, $R_{14}$ and $R_{15}$ are selected from among OH, $C_{2-10}$ alkanoyloxy and $C_{2-10}$ alkoxycarbonyloxy, particularly, those in which both $R_{11}$ and $R_{15}$ are H and at least two of the substituents $R_{12}$, $R_{13}$ and $R_{14}$ are selected from among OH, $C_{2-10}$ alkanoyloxy and $C_{2-10}$ alkoxycarbonyloxy. Specific examples include 3,4-diacetoxyphenyl, 3,4-dihydroxyphenyl, 3,5-diacetoxyphenyl, 3,5-dihydroxyphenyl, 3,4,5-triacetoxyphenyl, 3,4,5-trihydroxyphenyl and the like.

In the case where at least one of the substituents $R_{11}$, $R_{12}$, $R_{13}$, $R_{14}$ and $R_{15}$ is alkyl, at least one of the others is preferably selected from among OH, $C_{2-10}$ alkanoyloxy and $C_{2-20}$ alkoxycarbonyloxy. Those in which both $R_{11}$ and $R_{15}$ are H, at least one of the substituents $R_{12}$, $R_{13}$ and $R_{14}$ is alkyl, and at least one of the remainder is OH, $C_{2-10}$ alkanoyloxy or $C_{2-10}$ alkoxycarbonyloxy, for example, 3,5-dialkyl-4-hydroxyphenyl groups are more preferred. Specific examples include 3,5-di-tert-butyl-4-hydroxyphenyl group and the like. In the 3,5-dialkyl-4-hydroxyphenyl groups, the alkyl group is preferably branched and tert-butyl group is more preferred. In addition, those in which both $R_{11}$ and $R_{15}$ are H, one of the substituents $R_{12}$, $R_{13}$ and $R_{14}$ is alkyl, and the remaining two are selected from among OH, $C_{2-10}$ alkanoyloxy and $C_{2-10}$ alkoxycarbonyloxy are preferred. Specific examples include 3,5-diacetoxy-4-methylphenyl group and the like.

In the general formula (Ib), the atomic group represented by $R_4$ is preferably a group represented by the general formula (III). In the general formula (III), preferred substituents in the general formula (Ib) include those preferably selected as the substituents in the general formula (Ia). More specifically, at least one of the substituents $R_{11}$, $R_{12}$, $R_{13}$, $R_{14}$ and $R_{15}$ in the general formula (III) is preferably OH, $C_{2-10}$ alkanoyloxy, $C_{2-10}$ alkoxycarbonyloxy or $C_{1-4}$ alkoxy, more preferably, OH, $C_{2-10}$ alkanoyloxy or $C_{2-10}$ alkoxycarbonyloxy.

Those in which at least two of the substituents $R_{11}$, $R_{12}$, $R_{13}$, $R_{14}$ and $R_{15}$ are selected from among OH, $C_{2-10}$ alkanoyloxy and $C_{2-10}$ alkoxycarbonyloxy, particularly, those in which both $R_{11}$ and $R_{15}$ are H and at least two of the substituents $R_{12}$, $R_{13}$ and $R_{14}$ are selected from among OH, $C_{2-10}$ alkanoyloxy and $C_{2-10}$ alkoxycarbonyloxy are more preferred. Specific examples include 3,4-diacetoxyphenyl, 3,4-dihydroxyphenyl, 3,5-diacetoxyphenyl, 3,5-dihydroxyphenyl, 3,4,5-triacetoxyphenyl, 3,4,5-trihydroxyphenyl and the like.

In the case where at least one of the substituents $R_{11}$, $R_{12}$, $R_{13}$, $R_{14}$ and $R_{15}$ is alkyl, at least one of the others is preferably selected from among OH, $C_{2-10}$ alkanoyloxy and $C_{2-10}$ alkoxycarbonyloxy. Those in which both $R_{11}$ and $R_{15}$ are H, at least one of the substituents $R_{12}$, $R_{13}$ and $R_{14}$ is alkyl, and at least one of the remainder is OH, $C_{2-10}$ alkanoyloxy or $C_{2-10}$ alkoxycarbonyloxy are more preferred. In addition, those in which both $R_{11}$ and $R_{15}$ are H, one of the substituents $R_{12}$, $R_{13}$ and $R_{14}$ is alkyl, and the remaining two are OH, $C_{2-10}$ alkanoyloxy or $C_{2-10}$ alkoxycarbonyloxy are more preferred.

In the general formula (Ia), a group represented by the general formula (IV) is also preferred as the atomic group represented by $R_4$. Those in which at least one of the substituents $R_{21}$, $R_{22}$, $R_{23}$, $R_{24}$ and $R_{25}$ is selected from among OH, $C_{2-10}$ alkanoyloxy, $C_{2-10}$ alkoxycarbonyloxy and $C_{1-4}$ alkoxy, for example, 3,5-dimethoxystyryl group, are preferred. Furthermore, those in which at least one of the substituents $R_{21}$, $R_{22}$, $R_{23}$, $R_{24}$ and $R_{25}$ is selected from among OH, $C_{2-10}$ alkanoyloxy and $C_{2-10}$ alkoxycarbonyloxy are more preferred. Specific examples include 4-acetoxystyryl, 2-acetoxystyryl, 3-acetoxystyryl, 4-hydroxystyryl, 2-hydroxystyryl, 3-hydroxystyryl, 3,4-diacetoxystyryl, 3,4-dihydroxystyryl, 3,5-diacetoxystyryl, 3,5-dihydroxystyryl, 3,4,5-triacetoxystyryl, 3,4,5-trihydroxystyryl, 2,3-diacetoxystyryl, 2,3-dihydroxystyryl, 3,5-diacetoxy-4-methylstyryl and the like.

In addition, those in which at least two of the substituents $R_{21}$, $R_{22}$, $R_{23}$, $R_{24}$ and $R_{25}$ are selected from among OH, $C_{2-10}$ alkanoyloxy and $C_{2-10}$ alkoxycarbonyloxy, particularly, those in which both $R_{21}$ and $R_{25}$ are H and at least two of the substituents $R_{22}$, $R_{23}$ and $R_{24}$ are selected from among OH, $C_{2-10}$ alkanoyloxy and $C_{2-10}$ alkoxycarbonyloxy are more preferred. Specific examples include 3,4-diacetoxystyryl, 3,4-dihydroxystyryl, 3,5-diacetoxystyryl, 3,5-dihydroxystyryl, 3,4,5-triacetoxystyryl, 3,4,5-trihydroxystyryl and the like. Other more preferred examples include those in which a plurality of alkanoyloxy or alkoxycarbonyloxy groups bonded to the styryl group are partially hydrolyzed to convert to hydroxy group(s), as in the case of 3,4-diacetoxy-5-hydroxystyryl group.

In the case where at least one of the substituents $R_{21}$, $R_{22}$, $R_{23}$, $R_{24}$ and $R_{25}$ is alkyl, at least one of the others is preferably selected from among OH, $C_{2-10}$ alkanoyloxy and $C_{2-10}$ alkoxycarbonyloxy. Those in which both $R_{21}$ and $R_{25}$ are H, at least one of the substituents $R_{22}$, $R_{23}$ and $R_{24}$ is alkyl, and at least one of the remainder is OH, $C_{2-10}$ alkanoyloxy or $C_{2-10}$ alkoxycarbonyloxy, as in the case of 3,5-dialkyl-4-hydroxystyryl are more preferred. Specific examples include 3,5-dibutyl-4-hydroxystyryl group and the like. In the 3,5-dialkyl-4-hydroxystyryl groups, the alkyl group is preferably branched and tert-butyl group is more preferred. In addition, those in which both $R_{21}$ and $R_{25}$ are H, one of the substituents $R_{22}$, $R_{23}$ and $R_{24}$ is alkyl, and the remaining two are OH, $C_{2-10}$ alkanoyloxy or $C_{2-10}$ alkoxycarbonyloxy are preferred. Specific examples include 3,5-diacetoxy-4-methylstyryl group and the like.

Other preferred examples of the atomic group represented by $R_4$ include 1-methylcyclohexyl, 4-methylcyclohexyl, 4-oxo-4H-pyran-2-yl and 2-oxo-2H-pyran-5-yl and the like. The 4-methylcyclohexyl may have either cis- or trans-configuration.

The 1-arylpyrimidine derivatives (I) of the present invention are classified in a group of 1-arylpyrimidine derivatives represented by the general formula (Ia) whose pyrimidine ring is a uracil ring (2,4-dioxopyrimidine ring) (hereinafter designated as 1-aryluracil derivative compounds) and a group of 1-arylpyrimidine derivatives represented by the general formula (Ib) in which the pyrimidine ring (uracil ring) is condensed between the 5- and 6-positions to form an imidazole ring skeleton (hereinafter designated as 3-arylpurine derivative compounds). Examples of the preferred 1-aryluracil derivatives, namely 1-aryluracil derivatives represented by the general formula (Ia) in which at least one of the substituents Ar, $R_1$, $R_4$, $R_5$ and $R_6$ is a preferred one will be classified and illustrated hereinafter together with examples of the preferred 3-arylpurine derivatives, namely 3-arylpurine derivatives represented by the general formula (Ib) in which at least one of the substituents Ar, $R_1$, $R_4$ and $R_6$ is a preferred one.

Examples of the 1-aryluracil derivatives of the present invention will now be classified according to the selection of the substituents Ar, $R_1$, $R_4$, $R_5$ and $R_6$ and illustrated.

1-Aryluracil derivatives in which Ar is a substituted or unsubstituted phenyl group represented by the general formula (II) and $R_4$ is a substituted phenyl group represented by the general formula (III) are represented by the following general formula (V):

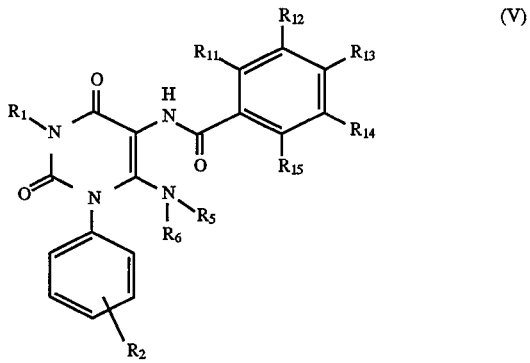

wherein $R_1$, $R_2$, $R_5$, $R_6$, $R_{11}$, $R_{12}$, $R_{13}$, $R_{14}$ and $R_{15}$ are as defined above.

Examples of the 1-aryluracil derivatives represented by the general formula (V) include 6-amino-5-(3,5-di-tert-butyl-4-hydroxyphenyl)carboxyamido-3-methyl-1-phenyluracil, 6-amino-5-(3,5-di-tert-butyl-4-hydroxyphenyl)carboxyamido-1-(4-fluorophenyl)-3-methyluracil, 6-amino-5-(3,5-di-tert-butyl-4-hydroxyphenyl)carboxyamido-3-methyl-1-(4-methylphenyl)uracil, 6-amino-5-(3,5-di-tert-butyl-4-hydroxyphenyl)carboxyamido-1-(4-methoxyphenyl)-3-methyluracil, 6-amino-5-(3,5-di-tert-butyl-4-hydroxyphenyl)carboxyamido-1-phenyl-3-propyluracil, 6-amino-3-benzyl-5-(3,5-di-tert-butyl-4-hydroxyphenyl)carboxyamido-1-phenyluracil, 6-amino-5-(3,5-diacetoxyphenyl)carboxyamido-3-methyl-1-phenyluracil, 6-amino-5-(3,5-diacetoxyphenyl)carboxyamido-1-(4-fluorophenyl)-3-methyluracil, 6-amino-5-(3,5-diacetoxyphenyl)carboxyamido-3-methyl-1-(4-methylphenyl)uracil, 6-amino-5-(3,5-diacetoxyphenyl)carboxyamido-1-(4-methoxyphenyl)-3-methyluracil, 6-amino-5-(3,5-diacetoxyphenyl)carboxyamido-1-phenyl-3-propyluracil, 6-amino-3-benzyl-5-(3,5-diacetoxyphenyl)carboxyamido-1-phenyluracil, 6-amino-5-(3,5-dimethoxyphenyl)carboxyamido-3-methyl-1-phenyluracil, 6-amino-5-(3,5-dihydroxyphenyl)carboxyamido-3-methyl-1-phenyluracil, 5-(3,5-diacetoxyphenyl)carboxyamido-3-methyl-6-methylamino-1-phenyluracil, 5-(3,5-diacetoxyphenyl)carboxyamido-6-methylamino-1-phenyl-3-propyluracil, 5-(3,5-diacetoxyphenyl)carboxyamido-6-dimethylamino-1-(4-fluorophenyl)-3-methyluracil, 6-amino-5-(3,5-diacetoxy-4-methylphenyl)carboxyamido-3-methyl-1-phenyluracil, 6-amino-1-(4-chlorophenyl)-5-(3,5-diacetoxyphenyl)carboxyamido-3-methyluracil, 6-amino-1-(2-chlorophenyl)-5-(3,5-diacetoxyphenyl)carboxyamido-3-methyluracil, 6-amino-1-(3-chlorophenyl)-5-(3,5-diacetoxyphenyl)carboxyamido-3-methyluracil, 6-amino-3-methyl-1-phenyl-5-(3,4,5-triacetoxyphenyl)carboxyamidouracil, 6-amino-1-(4-fluorophenyl)-3-methyl-5-(3,4,5-triacetoxyphenyl)carboxyamidouracil, 6-amino-1-(4-methoxyphenyl)-3-methyl-5-(3,4,5-triacetoxyphenyl)carboxyamidouracil, 6-amino-3-methyl-1-(4-methylphenyl)-5-(3,4,5-triacetoxyphenyl)carboxyamidouracil, 6-amino-1-phenyl-3-propyl-5-(3,4,5-triacetoxyphenyl)carboxyamidouracil, 6-amino-3-benzyl-1-phenyl-5-(3,4,5-triacetoxyphenyl)carboxyamidouracil, 3-methyl-6-methylamino-1-phenyl-5-(3,4,5-triacetoxyphenyl)carboxyamidouracil, 6-amino-3-methyl-1-phenyl-5-(3,4,5-trihydroxyphenyl)carboxyamidouracil, 6-dimethylamino-1-(4-fluorophenyl)-3-methyl-5-(3,4,5-triacetoxyphenyl)carboxyamidouracil, 6-amino-1-(4-chlorophenyl)-3-methyl-5-(3,4,5-triacetoxyphenyl)carboxyamidouracil, 6-amino-1-(2-chlorophenyl)-3-methyl-5-(3,4,5-triacetoxyphenyl)carboxyamidouracil, 6-amino-1-(3-chlorophenyl)-3-methyl-5-(3,4,5-triacetoxyphenyl)carboxyamidouracil, 6-amino-5-(3,4-diacetoxyphenyl)carboxyamido-3-methyl-1-phenyluracil, 6-amino-5-(3,4-diacetoxyphenyl)carboxyamido-1-(4-fluorophenyl)-3-methyluracil, 6-amino-5-(3,4-diacetoxyphenyl)carboxyamido-3-methyl-1-(4-methylphenyl)uracil, 6-amino-5-(3,4-diacetoxyphenyl)carboxyamido-1-(4-methoxyphenyl)-3-methyluracil, 6-amino-5-(3,4-diacetoxyphenyl)carboxyamido-1-phenyl-3-propyluracil, 6-amino-3-benzyl-5-(3,4-diacetoxyphenyl)carboxyamido-1-phenyluracil, 6-amino-5-(3,4-dihydroxyphenyl)carboxyamido-3-methyl-1-phenyluracil, 5-(3,4-diacetoxyphenyl)carboxyamido-3-methyl-6-methylamino-1-phenyluracil, 5-(3,4-diacetoxyphenyl)carboxyamido-6-methylamino-1-phenyl-3-propyluracil, 5-(3,4-diacetoxyphenyl)carboxyamido-6-dimethylamino-1-(4-fluorophenyl)-3-methyluracil, 6-amino-1-(4-chlorophenyl)-5-(3,4-diacetoxyphenyl)carboxyamido-3-methyluracil, 6-amino-1-(2-chlorophenyl)-5-(3,4-diacetoxyphenyl)carboxyamido-3-methyluracil, 6-amino-1-(3-chlorophenyl)-5-(3,4-diacetoxyphenyl)carboxyamido-3-methyluracil, 5-(4-acetoxy-3-methoxyphenyl)carboxyamido-6-amino-3-methyl-1-phenyluracil, 5-(3-acetoxy-4-methoxyphenyl)carboxyamido-6-amino-3-methyl-1-phenyluracil, 6-amino-5-(2-hydroxy-5-methoxyphenyl)carboxyamido-3-methyl-1-phenyluracil, 6-amino-1-(4-fluorophenyl)-5-(2-hydroxy-5-methoxyphenyl)carboxyamido-3-methyluracil, 5-(2-acetoxy-5-methoxyphenyl)carboxyamido-6-amino-1-(4-methoxyphenyl)-3-methyluracil, 5-(2-acetoxyphenyl)carboxyamido-6-amino-3-methyl-1-phenyluracil, 5-(3-acetoxyphenyl)carboxyamido-6-amino-3-methyl-1-phenyluracil, 5-(4-acetoxyphenyl)carboxyamido-6-amino-3-methyl-1-phenyluracil, 6-amino-5-(2,3-diacetoxyphenyl)carboxyamido-3-methyl-1-phenyluracil, 6-amino-5-(2,3-diacetoxyphenyl)carboxyamido-1-(4-fluorophenyl)-3-methyluracil, 6-amino-5-(2,3-diacetoxyphenyl)carboxyamido-3-methyl-1-(4-methylphenyl)uracil, 6-amino-5-(2,3-diacetoxyphenyl)carboxyamido-1-(4-methoxyphenyl)-3-methyluracil, 5-(3-acetoxy-5-hydroxyphenyl)carboxyamido-6-amino-3-methyl-1-phenyluracil and the like.

The compounds in which at least one of the substituents $R_{11}$, $R_{12}$, $R_{13}$, $R_{14}$ and $R_{15}$ is methoxy, OH or acetoxy are preferred. More preferred are those in which $R_5$ or $R_6$ is H, that is, compounds having an amino or a monoalkyl-substituted amino group at the 6-position of the uracil ring. Still more preferred are those in which at least two of $R_{11}$, $R_{12}$, $R_{13}$, $R_{14}$ and $R_{15}$ are OH or acetoxy, particularly, those in which at least two of $R_{12}$, $R_{13}$ and $R_{14}$ are OH or acetoxy and both $R_{11}$ and $R_{15}$ are H, as exemplified by the group of compounds having 3,4-diacetoxyphenyl, 3,4-dihydroxyphenyl, 3,5-diacetoxyphenyl, 3,5-dihydroxyphenyl, 3,4,5-triacetoxyphenyl or 3,4,5-trihydroxyphenyl group.

In addition, preferred 1-aryluracil derivatives are those in which both $R_5$ and $R_6$ are H, Ar is a substituted or unsubstituted phenyl group represented by the general formula (II) and $R_4$ is a substituted styryl group represented by the general formula (IV). These 1-aryluracil derivatives are represented by the following general formula (VI):

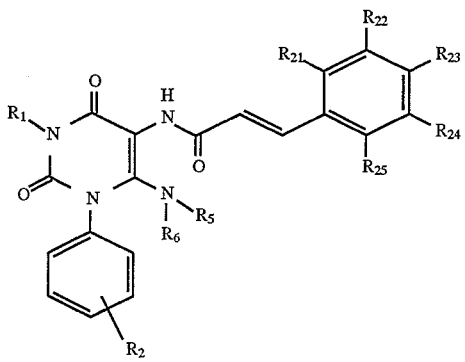

(VI)

wherein $R_1$, $R_2$, $R_5$, $R_6$, $R_{21}$, $R_{22}$, $R_{23}$, $R_{24}$ and $R_{25}$ are as defined above.

Examples of the 1-aryluracil derivatives represented by the general formula (VI) include 6-amino-5-(3,4-diacetoxystyryl)carboxyamido-3-methyl-1-phenyluracil, 5-(4-acetoxy-3-methoxystyryl)carboxyamido-6-amino-3-methyl-1-phenyluracil, 6-amino-5-(3,5-diacetoxystyryl) carboxyamido-3-methyl-1-phenyluracil, 6-amino-5-(3,4-dihydroxystyryl)carboxyamido-3-methyl-1-phenyluracil, 6-amino-5-(3,5-dihydroxystyryl)carboxyamido-3-methyl-1-phenyluracil, 6-amino-3-methyl-1-phenyl-5-(3,4,5-triacetoxystyryl)carboxyamidouracil, 6-amino-3-methyl-1-phenyl-5-(3,4,5-trihydroxystyryl)carboxyamidouracil and the like.

The compounds in which at least one of the substituents $R_{21}$, $R_{22}$, $R_{23}$, $R_{24}$ and $R_{25}$ is methoxy, OH or acetoxy are preferred. More preferred are those in which at least two of $R_{21}$, $R_{22}$, $R_{23}$, $R_{24}$ and $R_{25}$ are OH or acetoxy, particularly, those in which at least two of $R_{22}$, $R_{23}$ and $R_{24}$ are OH or acetoxy and both $R_{21}$ and $R_{25}$ are H, as exemplified by the group of compounds having a substituted styryl group such as 3,4-diacetoxystyryl, 3,4-dihydroxystyryl, 3,5-diacetoxystyryl, 3,5-dihydroxystyryl, 3,4,5-triacetoxystyryl or 3,4,5-trihydroxystyryl group.

Other preferred examples are 1-aryluracil derivatives in which both $R_5$ and $R_6$ are H, Ar is a substituted or unsubstituted phenyl group represented by the general formula (II) and $R_4$ is 4-oxo-4H-pyran-2-yl or 2-oxo-2H-pyran-5-yl. These 1-aryluracil derivatives are represented by the following general formula (VII) or (VIII):

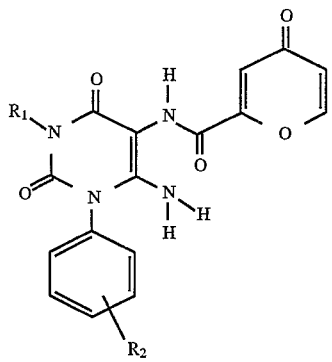

(VII)

wherein $R_1$ and $R_2$ are as defined above.

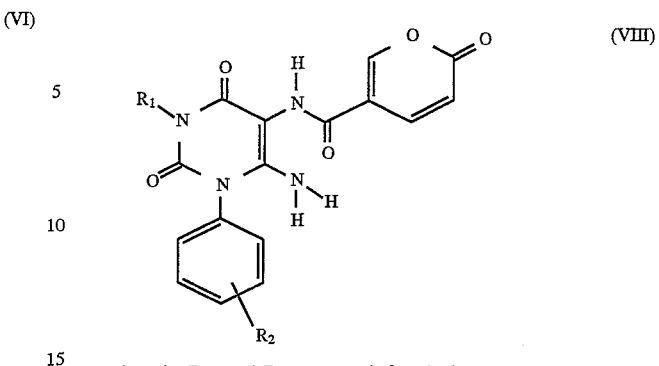

(VIII)

wherein $R_1$ and $R_2$ are as defined above.

Examples of the 1-aryluracil derivatives represented by the general formula (VII) or (VIII) include 6-amino-3-methyl-5-(4-oxo-4H-pyran-2-yl)carboxyamido-1-phenyluracil, 6-amino-3-methyl-5-(2-oxo-2H-pyran-5-yl)carboxyamido-1-phenyluracil and the like.

Other preferred examples are 1-aryluracil derivatives in which both $R_5$ and $R_6$ are H, Ar is a substituted or unsubstituted phenyl group represented by the general formula (II) and $R_4$ is 4-methylcyclohexyl or 1-methylcyclohexyl. These 1-aryluracil derivatives are represented by the following general formula (IX) or (X):

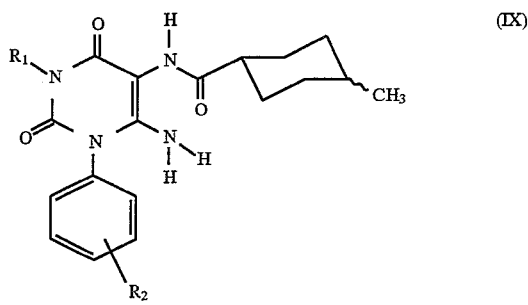

(IX)

wherein $R_1$ and $R_2$ are as defined above.

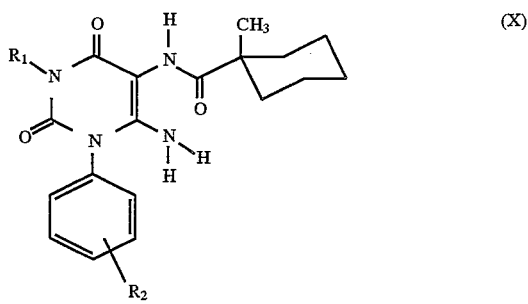

(X)

wherein $R_1$ and $R_2$ are as defined above.

Examples of the 1-aryluracil derivatives represented by the general formula (IX) or (X) include 6-amino-3-methyl-5-(4-methylcyclohexyl)carboxyamido-1-phenyluracil, 6-amino-3-methyl-5-(1-methylcyclohexyl)carboxyamido-1-phenyluracil and the like. The 4-methylcyclohexyl may have either cis- or trans-configuration.

Other preferred examples are 1-aryluracil derivatives in which both $R_5$ and $R_6$ are H, Ar is 1-naphthyl and $R_4$ is a substituted phenyl group represented by the general formula (III). These 1-aryluracil derivatives are represented by the following general formula (XI):

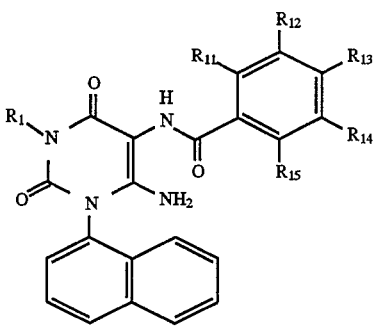

wherein $R_1$, $R_{11}$, $R_{12}$, $R_{13}$, $R_{14}$ and $R_{15}$ are as defined above.

Examples of the 1-aryluracil derivatives represented by the general formula (XI) include 6-amino-5-(3,5-diacetoxyphenyl)carboxyamido-3-methyl-1-(1-naphthyl) uracil, 6-amino-5-(3,4-diacetoxyphenyl)carboxyamido-3-methyl-1-(1-naphthyl)uracil, 6-amino-5-(3,5-dihydroxyphenyl)carboxyamido-3-methyl-1-(1-naphthyl) uracil, 6-amino-5-(3,4-dihydroxyphenyl)carboxyamido-3-methyl-1-(1-naphthyl)uracil, 6-amino-3-methyl-1-(1-naphthyl)-5-(3,4,5-triacetoxyphenyl)carboxyamidouracil, 6-amino-3-methyl-1-(1-naphthyl)-5-(3,4,5-trihydroxyphenyl)carboxyamidouracil and the like. Preferred are those in which at least two of $R_{11}$, $R_{12}$, $R_{13}$, $R_{14}$ and $R_{15}$ are OH or acetoxy, particularly, those in which at least two of $R_{12}$, $R_{13}$ and $R_{14}$ are OH or acetoxy and both $R_{11}$ and $R_{15}$ are H, as exemplified by the group of compounds having 3,4-diacetoxyphenyl, 3,4-dihydroxyphenyl, 3,5-diacetoxyphenyl, 3,5-dihydroxyphenyl, 3,4,5-triacetoxyphenyl or 3,4,5-trihydroxyphenyl group.

Examples of the preferred 1-aryluracil derivatives which are classified in different groups have been illustrated above by showing their structures and compound names but the 1-aryluracil derivatives of the present invention are not limited to these examples. The compounds represented by the general formula (Ia) in which at least one of Ar, $R_1$, $R_4$, $R_5$ and $R_6$ is selected from among the preferred atoms or groups are also preferred. Those in which more than one of Ar, $R_1$, $R_4$, $R_5$ and $R_6$ are selected from among the preferred atoms or groups are more preferred.

Examples of the 3-arylpurine derivatives of the present invention will now be classified according to the selection of the substituents Ar, $R_1$, $R_4$ and $R_6$ and illustrated.

3-Arylpurine derivatives in which $R_6$ is H, Ar is a substituted or unsubstituted phenyl group represented by the general formula (II) wherein $R_2$ is present at the p-position are represented by the following general formula (XII):

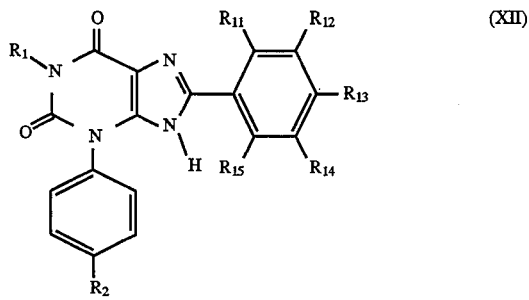

wherein $R_1$, $R_2$, $R_{11}$, $R_{12}$, $R_{13}$, $R_{14}$ and $R_{15}$ are as defined above.

In particular, 3-arylpurine derivatives in which $R_4$ is a substituted-phenyl group represented by the general formula (III) wherein both $R_{11}$ and $R_{15}$ are H and at least one of $R_{12}$, $R_{13}$ and $R_{14}$ is not H are represented by the following general formula (XIII):

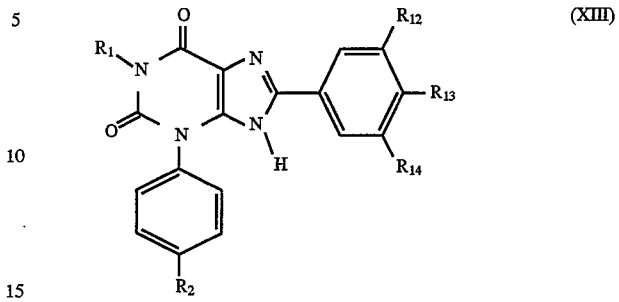

wherein $R_1$, $R_2$, $R_{12}$, $R_{13}$ and $R_{14}$ are as defined above.

Examples of the 3-arylpurine derivatives represented by the general formula (XII) or (XIII) include 8-(3,4-dihydroxyphenyl)-1-methyl-3-phenylpurine-2,6-dione, 8-(3,5-dihydroxyphenyl)-1-methyl-3-phenylpurine-2,6-dione, 1-methyl-3-phenyl-8-(3,4,5-triacetoxyphenyl)purine-2,6-dione, 8-(3,5-diacetoxyphenyl)-1-methyl-3-phenylpurine-2,6-dione, 1-methyl-3-phenyl-8-(3,4,5-trihydroxyphenyl)purine-2,6-dione, 8-(3,5-dibutyl-4-hydroxyphenyl)-1-methyl-3-phenylpurine-2,6-dione, 8-(3,5-dibutyl-4-hydroxyphenyl)-3-(4-methoxyphenyl)-1-methylpurine-2,6-dione, 8-(3,5-dibutyl-4-hydroxyphenyl)-1-methyl-3-(4-methylphenyl)purine-2,6-dione, 8-(3,5-dibutyl-4-hydroxyphenyl)-3-(4-fluorophenyl)-1-methylpurine-2,6-dione, 8-(3,5-di-tert-butyl-4-hydroxyphenyl)-1-methyl-3-phenylpurine-2,6-dione, 8-(3,5-di-tert-butyl-4-hydroxyphenyl)-3-(4-methoxyphenyl)-1-methylpurine-2,6-dione, 8-(3,5-di-tert-butyl-4-hydroxyphenyl)-1-methyl-3-(4-methylphenyl)purine-2,6-dione, 8-(3,5-di-tert-butyl-4-hydroxyphenyl)-3-(4-fluorophenyl)-1-methylpurine-2,6-dione and the like.

In addition, examples of the more preferred compounds, namely 3-arylpurine derivatives represented by the general formula (XIII) wherein at least two of $R_1$, $R_2$, $R_{12}$, $R_{13}$ and $R_{14}$ are selected from among the preferred atoms or groups will be classified and illustrated hereinafter.

More preferred examples of the 3-arylpurine derivatives represented by the general formula (XIII) wherein $R_1$ is methyl and at least two of $R_{12}$, $R_{13}$ and $R_{14}$ are OH or acetoxy, more specifically, $R_4$ is 3,4-dihydroxyphenyl, 3,4-diacetoxyphenyl, 3,5-dihydroxyphenyl, 3,5-diacetoxyphenyl, 3,4,5-trihydroxyphenyl or 3,4,5-triacetoxyphenyl include 8-(3,4-dihydroxyphenyl)-1-methyl-3-phenylpurine-2,6-dione, 8-(3,5-dihydroxyphenyl)-1-methyl-3-phenylpurine-2,6-dione, 1-methyl-3-phenyl-8-(3,4,5-triacetoxyphenyl)purine-2,6-dione, 8-(3,5-diacetoxyphenyl)-1-methyl-3-phenylpurine-2,6-dione, 1-methyl-3-phenyl-8-(3,4,5-trihydroxyphenyl)purine-2,6-dione and the like.

Other more preferred examples are the 3-arylpurine derivatives represented by the general formula (XIII) wherein $R_1$ is methyl, $R_{13}$ is OH, and both $R_{12}$ and $R_{14}$ are alkyl, more preferably branched alkyl, that is, $R_4$ is 3,5-dialkyl-4-hydroxyphenyl, more preferably 3,5-di-tert-butyl-4-hydroxyphenyl. Examples include 8-(3,5-di-tert-butyl-4-hydroxyphenyl)-1-methyl-3-phenylpurine-2,6-dione, 8-(3,5-di-tert-butyl-4-hydroxyphenyl)-3-(4-methoxyphenyl)-1-methylpurine-2,6-dione, 8-(3,5-di-tert-butyl-4-hydroxyphenyl)-1-methyl-3-(4-methylphenyl)purine-2,6-dione, 8-(3,5-di-tert-butyl-4-hydroxyphenyl)-3-(4-fluorophenyl)-1-methylpurine-2,6-dione and the like.

The compounds in which the substituents $R_1$, $R_2$, $R_{12}$, $R_{13}$ and $R_{14}$ are all selected from among the preferred atoms or groups become more preferable if the substituent $R_2$ is selected from H, methyl, methoxy or fluorine.

Examples of the preferred 3-aryluracil derivatives which are classified in different groups have been illustrated above by showing their structures and compound names but the 3-arylpurine derivatives of the present invention are not limited to these examples. The compounds represented by the general formula (Ib) in which at least one of Ar, $R_1$, $R_4$ and $R_6$ is selected from among the preferred atoms or groups are also preferred. Those in which more than one of Ar, $R_1$, $R_4$ and $R_6$ are selected from among the preferred atoms or groups are more preferred.

Schemes of preparing the 1-arylpyrimidine derivatives (I) of the present invention, that is, the group of the 1-aryluracil derivatives represented by the general formula (Ia) and that of the 3-arylpurine derivatives represented by the general formula (Ib) will now be described separately.

The synthesis of the 1-aryluracil derivatives represented by the general formula (Ia) of the present invention starts with isocyanates having an aryl group substituent (Ar) on the nitrogen atom at the 1-position of the uracil ring and they can be produced by the following method.

Step 1 [Preparation of urea derivatives]

Isocyanates represented by general formula (XIV):

  (XIV)

wherein Ar is as defined above,
are reacted with primary amines represented by general formula (XV):

  (XV)

wherein $R_1$ is as defined above,
to prepare urea derivatives represented by general formula (XVI):

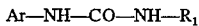  (XVI)

wherein Ar and $R_1$ are as defined above.

Reaction temperature is desirably selected from between room temperature and about 80° C. The reaction is suitably conducted in the absence of solvents or in aprotic solvents such as THF, 1,4-dioxane, toluene and the like. If $R_1$ is H (when ammonia is used), it is preferred to dissolve ammonia in a solvent before the reaction is started.

Step 2 [Formation of uracil ring]

The urea derivatives represented by the general formula (XVI) are reacted with cyanoacetic acid to prepare 6-aminouracil derivatives represented by general formula (XVII):

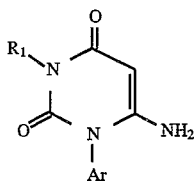  (XVII)

wherein Ar and $R_1$ are as defined above.

The reaction is suitably conducted in a dehydrating solvent such as an acid anhydride like acetic anhydride. Reaction temperature is desirably selected from between room temperature and the reflux temperature of the solvent.

When a mono- or di-substituted amino group is selected as a substituent at the 6-position of the uracil ring in the 1-aryluracil derivatives represented by the general formula (Ia), 6-(substituted amino)uracil derivatives represented by general formula (XVIII):

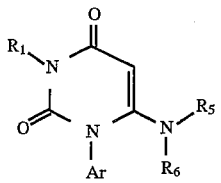  (XVIII)

wherein Ar, $R_1$, $R_5$ and $R_6$ are as defined above, provided that both $R_5$ and $R_6$ are not H, can be prepared from the 6-aminouracil derivatives of the general formula (XVII) by the following method.

An amino group at the 6-position of the 6-aminouracil derivative represented by the general formula (XVII) can be replaced with a hydroxy group using a protonic acid such as hydrochloric acid, sulfuric acid of the like to prepare 6-hydroxyuracil derivatives represented by general formula (XIX):

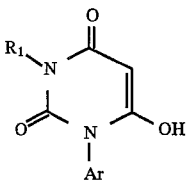  (XIX)

wherein Ar and $R_1$ are as defined above.

A hydroxyl group at the 6-position of the 6-hydroxyuracil derivative represented by the general formula (XIX) can then be replaced with a chlorine atom using a chlorinating agent, preferably, phosphorus pentachloride, phosphoryl chloride or the like to prepare 6-chlorouracil derivatives represented by general formula (XX):

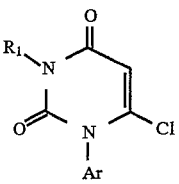  (XX)

wherein Ar and $R_1$ are as defined above.

The 6-chlorouracil derivatives represented by the general formula (XX) can be reacted with primary or secondary amines represented by general formula (XXI):

  (XXI)

wherein $R_5$ and $R_6$ are as defined above, provided that both $R_5$ and $R_6$ are not H, to prepare the 6-(substituted amino)uracil derivatives represented by the general formula (XVIII).

Step 3 [Introduction of an amino group into the 5-position of the uracil ring]

A nitroso group is introduced into the 5-position of the uracil ring by reacting the 6-aminouracil derivatives of the general formula (XVII) with sodium nitrite. The nitroso group is then reduced with $H_2$ to prepare 5,6-diaminouracil derivatives represented by general formula (XXII):

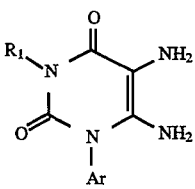

(XXII)

wherein Ar and $R_1$ are as defined above.

The nitrosation reaction is desirably conducted using a solvent such as water at a reaction temperature selected from between room temperature and the reflux temperature of the solvent. The reduction reaction with $H_2$ can be conducted using an alcohol solvent such as methanol in the presence of Pd/C by blowing hydrogen gas. Reaction temperature can be selected from between room temperature and the reflux temperature of the solvent, preferably about 70° C.

When the group at the 6-position of the uracil ring is a mono-substituted amino group in the 6-(substituted amino) uracil derivatives represented by the general formula (XVIII), a nitroso group is introduced into the 5-position of the uracil ring by reacting the 6-aminouracil derivatives of the general formula (XVII) with sodium nitrite by the same method as mentioned above. The nitroso group is then reduced with $H_2$ to prepare corresponding 6-(mono-substituted amino)-5-aminouracil derivatives represented by general formula (XXIII):

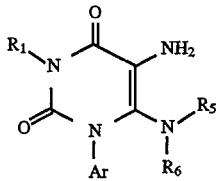

(XXIII)

wherein Ar, $R_1$, $R_5$ and $R_6$ are as defined above, provided that both $R_5$ and $R_6$ are not H.

When the group at the 6-position of the uracil ring is a di-substituted amino group in the 6-(substituted amino) uracil derivatives represented by the general formula (XVIII), a nitro group is introduced into the 5-position of the uracil ring by treating the 6-aminouracil derivatives of the general formula (XVII) with a mixed acid prepared from sulfuric acid and nitric acid. The nitro group is then reduced with $H_2$ to prepare corresponding 6-(di-substituted amino)-5-aminouracil derivatives represented by the general formula (XXIII).

Step 4 [Acylation of an amino group substituent at the 5-position of the uracil ring]

A carboxylic acid represented by general formula, $R_4$—COOH (wherein $R_4$ is the same as defined for the 1-aryluracil derivatives represented by the general formula (Ia)), is reacted with thionyl chloride to prepare a corresponding acid chloride represented by general formula, $R_4$—COCl. The 6-(substituted amino)-5-aminouracil derivatives represented by the general formula (XXIII) can be reacted with the acid chloride to prepare the 1-aryluracil derivatives of the present invention as represented by the general formula (Ia) in which the amino group substituent at the 5-position of the uracil ring is acylated. Alternatively, the 5,6-diaminouracil derivatives represented by the general formula (XXII) can be reacted with the acid chloride to prepare the 1-aryluracil derivatives of the present invention as represented by the general formula (Ia) in which only the amino group substituent at the 5-position of the uracil ring is acylated.

The acylation reaction is preferably conducted using a solvent that will not readily react with the acid chloride, for example, a halogenated hydrocarbon solvent such as chloroform, dichloromethane or the like, an aromatic hydrocarbon solvent such as toluene or the like, or N,N-dimethylformamide or the like. Reaction temperature is desirably selected from between room temperature and the reflux temperature of the solvent.

In the 1-aryluracil derivatives of the present invention as represented by the general formula (Ia) which are prepared by the sequence of Steps 1–4, the substituents Ar, $R_1$, $R_4$, $R_5$ and $R_6$ are derived from raw material compounds and therefore any desired groups can be introduced. The compounds having these substituents can be identified easily and clearly by measuring mass analysis spectra, as well as $^1$H-NMR spectra characteristic of the substituents Ar, $R_1$, $R_4$, $R_5$ and $R_6$ according to conventional techniques.

The following reference examples demonstrate the preparation, by the sequence of Steps 2 and 3, of the 5,6-diaminouracil derivative represented by the general formula (XXII) and the 6-(substituted amino)-5-aminouracil derivative represented by the general formula (XXIII).

REFERENCE EXAMPLE 1

Preparation of 5,6-diamino-3-methyl-1-phenyluracil

N-Methyl-N'-phenylurea was preliminarily prepared from phenyl isocyanate and methylamine by the procedure described in Step 1. Using the urea compound as the starting material, uracil ring was formed by the procedure described in Step 2. N-Methyl-N'-phenylurea (30 g, 0.2M) and cyanoacetic acid (18.8 g, 0.22M) were dissolved in 400 ml of a solvent, acetic anhydride, and heated at 80° C. for 2 hours. The solvent acetic anhydride was distilled off under reduced pressure and 200 ml of water was added to the residue, followed by cooling with ice. A 2N aqueous solution of NaOH (220 ml) was then added and the mixture was stirred for 2 hours. A precipitated solid product was obtained by filtration. The solid product was washed successively with water and methanol and dried to yield 6-amino-3-methyl-1-phenyluracil (yield: 33 g, or 76% based on N-methyl-N'-phenylurea).

The obtained 6-amino-3-methyl-1-phenyluracil (24 g, 0.11M) and NaOH (2.8 g, 70 mM) were dissolved in 110 ml of water. To the resulting solution was added dropwise an aqueous solution of sodium nitrite (9.5 g/80 ml). Acetic acid (13 ml) was then added dropwise at 0° C. and the mixture was brought to room temperature, followed by stirring for 2 hours. A precipitated solid product was obtained by filtration. The solid product was washed successively with water and methanol and dried to yield 6-amino-3-methyl-5-nitroso-1-phenyluracil (yield: 27 g, or 99% based on 6-amino-3-methyl-1-phenyluracil).

The obtained 6-amino-3-methyl-5-nitroso-1-phenyluracil (0.25 g) and 5% Pd/C (20 mg) were added to 50 ml of methanol and purging with hydrogen gas was performed, followed by stirring at 70° C. for 2.5 hours. The reaction mixture was filtered while hot to give a filtrate. The solvent methanol was distilled off from the filtrate to yield 5,6-diamino-3-methyl-1-phenyluracil (yield: 0.2 g, or 86% based on 6-amino-3-methyl-5-nitroso-1-phenyluracil).

REFERENCE EXAMPLE 2

Preparation of 5-amino-3-methyl-6-methylamino-1-phenyluracil

6-Amino-3-methyl-1-phenyluracil as obtained in Reference Example 1 (8.7 g, 40 mM) was dissolved in 80 ml of acetic acid and hydrochloric acid (16 ml) was added, followed by heating at 100° C. for 1 hour. The solvent acetic acid was then distilled off under reduced pressure and water war added to the residue. The pH of the resulting solution was adjusted to 1 by adding hydrochloric acid and a product was extracted with dichloromethane. After the solvent dichloromethane was distilled off under reduced pressure from the dichloromethane layer, crystallization with ethanol was performed to give 6-hydroxy-3-methyl-1-phenyluracil (yield: 5.9 g, or 68% based on 6-amino-3-methyl-1-phenyluracil).

To the obtained 6-hydroxy-3-methyl-1-phenyluracil (12.2 g, 56 mM) was added phosphorus oxychloride (phosphoryl chloride, 167 ml, 2M) under cooling with ice and 3.4 ml of water was then added dropwise. The solution was heated gradually and maintained at 110° C. for 2 hours. The solvent was distilled off under reduced pressure. A product was obtained by crystallization with water and recovered by filtration to yield 6-chloro-3-methyl-1-phenyluracil (yield: 9.55 g, or 72% based on 6-hydroxy-3-methyl-1-phenyluracil).

The obtained 6-chloro-3-methyl-1-phenyluracil (4.26 g, 18 mM) was added to 100 ml of 2-propanol. A 40% aqueous solution of methylamine (17 g, 0.22M) was added to the resulting solution and the mixture was heated at 90° C. for 5 hours while stirring. After being left to cool, a precipitated crystal was obtained by filtration and washed successively with ethanol and water to yield 3-methyl-6-methylamino-1-phenyluracil (yield: 3.71 g, or 89% based on 6-chloro-3-methyl-1-phenyluracil).

Thereafter, the nitrosation and reduction at the 5-position of the uracil ring were performed by the same procedure as in Reference Example 1 to yield 5-amino-3-methyl-6-methylamino-1-phenyluracil.

The 5,6-diaminouracil derivatives represented by the general formula (XXII) and the 6-(substituted amino)-5-aminouracil derivatives represented by the general formula (XXIII), which are prepared by the same procedure as in Reference Examples 1 and 2, are desirably used in Step 4 after being further purified as required.

A method of preparing the group of the 3-arylpurine derivatives of the present invention as represented by the general formula (Ib) will now be described.

Step 5 [Introduction of an amino group into the 5-position of the uracil ring]

5,6-Diamino-1-(substituted or unsubstituted phenyl) uracil derivatives represented by general formula (XXIV):

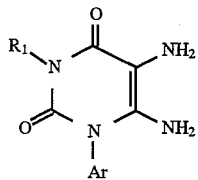
(XXIV)

wherein Ar is a substituted or unsubstituted phenyl group represented by the general formula (II) and $R_1$ is as defined above, or 5-amino-6-(mono-substituted amino)-1-(substituted or unsubstituted phenyl)uracil derivatives represented by general formula (XXV):

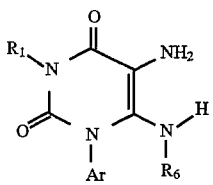
(XXV)

wherein Ar is a substituted or unsubstituted phenyl group represented by the general formula (II) and $R_1$ and $R_6$ are as defined above, are respectively prepared by the procedures described in Steps 1–3.

Step 6 [Formation of purine nuclear skeleton]

The amino group at the 5-position of the uracil ring was iminated by reacting the 5,6-diamino-1-(substituted or unsubstituted phenyl)uracil derivatives of the general formula (XXIV) or 5-amino-6-(mono-substituted amino)-1-(substituted or unsubstituted phenyl)uracil derivatives of the general formula (XXV) with a benzaldehyde derivative represented by general formula (XXVI):

$R_4$—CHO (XXVI)

wherein $R_4$ is a substituted phenyl group represented by the general formula (III), to prepare benzylideneamine derivatives represented by general formula (XXVII):

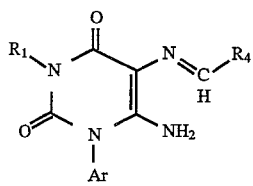
(XXVII)

wherein Ar is a substituted or unsubstituted phenyl group represented by the general formula (II), $R_4$ is a substituted phenyl group represented by the general formula (III) and $R_1$ is as defined above, or general formula (XXVIII):

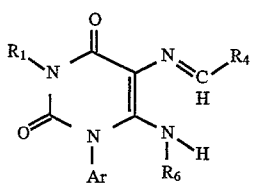
(XXVIII)

wherein Ar is a substituted or unsubstituted phenyl group represented by the general formula (II), $R_4$ is a substituted phenyl group represented by the general formula (III) and $R_1$ and $R_6$ are as defined above. This condensation reaction is desirably conducted using an alcohol solvent such as methanol, ethanol or the like at a reaction temperature selected from between room temperature and the reflux temperature of the solvent.

Subsequently, purine nuclear skeletons are formed by the ring closure of the benzylideneamine derivatives to prepare a group of the 3-arylpurine derivatives of the present invention as represented by the general formula (Ib). The ring closure reaction is preferably conducted using thionyl chloride at a reaction temperature selected from between room temperature and the reflux temperature of the solvent, particularly at the reflux temperature of the solvent.

In the 3-arylpurine derivatives of the present invention as represented by the general formula (Ib) which are prepared by the sequence of Steps 5 (Steps 1–3) and 6, the substituents Ar, $R_1$, $R_4$ and $R_6$ are derived from raw material compounds and therefore any desired groups can be introduced. The compounds having these substituents can be identified easily and clearly by measuring mass analysis spectra, as well as $^1$H-NMR spectra characteristic of the substituents Ar, $R_1$, $R_4$ and $R_6$ according to conventional techniques.

Preferred examples of the pharmaceutically acceptable salts of the 1-arylpyrimidine derivatives of the present invention as represented by the general formula (I) which encompass the 1-aryluracil derivatives of the general formula (Ia) and 3-arylpurine derivatives of the general formula (Ib) include salts with pharmaceutically acceptable acids. Illustrative examples of the pharmaceutically acceptable salts include hydrochlorides, sulfates, acetates, hydrobromides, phosphates, succinates, malates, fumarates, citrates, gluconates, methanesulfonates, p-toluenesulfonates and the like. When a phenolic hydroxyl group is present in the 1-aryluracil derivatives, their sodium salts or potassium salts are also preferred examples of the pharmacemutically acceptable salts.

As shown in the Experimental Examples for verifying an inhibiting effect on each of type IV and type I allergies, the 1-arylpyrimidine derivatives of the present invention which are represented by the general formula (I) exhibit good drug efficacy against both allergies of types I and IV in oral administration. Hence, these compounds can be used as effective therapeutic agents of allergic diseases, particularly type I allergy characterized by great contribution from type IV allergy and a mixed allergy of types I and IV. Specifically, they are useful as therapeutic agents for inhibiting or alleviating asthma, allergic diseases that have manifestations of inflammations such as dermatitis or rhinitis, for example, atopic dermatitis, symptoms such as bronchoconstriction accompanied by asthma, and allergic diseases such as graft-versus-host disease (GVHD) that develops after organ transplantation. Additionally, being low-molecular weight non-steroid compounds, they can be administered orally and cause no severe and diverse side effects such as infectious diseases, osteoporosis and the like as observed broadly in steroid agents and are therefore preferably used in long term administration.

When pharmaceutical compositions comprising the 1-arylpyrimidine derivative (I) of the present invention or pharmaceutically acceptable salt thereof as an active ingredient are used specifically as therapeutic agents of asthma-accompanied bronchoconstriction, atopic dermatitis, allergic diseases or graft-versus-host disease, they are administered usually in the form of oral preparations such as capsules, tablets, fine granules, granules, powders, syrups or the like, or injections. These preparations can be formulated with pharmacologically or pharmaceutically acceptable additives by conventional methods. In oral preparations, pharmaceutical additives including vehicles such as D-mannitol, lactose and starch, disintegrants such as carboxymethyl cellulose, binders such as polyvinylpyrrolidone and hydroxypropyl cellulose, lubricants such as magnesium stearate and talc can be used to yield desired dosage forms. In injections, pharmaceutical additives including solution adjuvants such as distilled water for injection and physiological saline, tonicity agents, pH modifiers can be used.

The dose of the 1-arylpyrimidine derivatives or pharmaceutically acceptable salts thereof according to the present invention should be selected as appropriate for depending the sex and age of individual patients, severity of the disease to be treated and the like. In the case of adult patients, the dose is preferably selected from the range of from about 1 to about 100 mg/kg per day for oral administration.

The 1-arylpyrimidine derivatives of the present invention have excellent biological activity for inhibiting each of type I and IV allergies. Hence, these compounds can be used as effective therapeutic agents of a wide variety of allergic diseases classified as allergies of types I and IV. Additionally, the 1-arylpyrimidine derivatives of the present invention are low-molecular weight non-steroid compounds, so they have the advantage of causing little or no side effects as observed broadly in steroid agents and, hence are suitable for use as therapeutic agents of allergic diseases in long-term and continuous administration. This advantage is particularly remarkable when they are used as therapeutic agents of type I allergy characterized by great contribution from type IV allergy and a mixed allergy of types I and IV, more specifically, as oral therapeutic agents for inhibiting or alleviating asthma, allergic diseases that have manifestations of inflammations such as dermatitis or rhinitis, for example, atopic dermatitis, symptoms such as bronchoconstriction accompanied by asthma, and allergic diseases such as graft-versus-host disease (GVHD) that develops after organ transplantation.

DESCRIPTION OF THE PREFERRED EMBODIMENTS

The present invention will now be explained in greater detail with reference to the following examples and experimental examples, which are not intended to limit the scope of the invention.

EXAMPLE 1

6-Amino-5-(3,5-di-tert-butyl-4-hydroxyphenyl) carboxyamido-3-methyl-1-phenyluracil 4-Hydroxy-3,5-di-tert-butyl benzoic acid (12.5 g, 50 mM) was dissolved in 80 ml of chloroform. To the resulting solution was added dropwise a solution of $SOCl_2$ (chlorination agent, 10 ml) in chloroform (20 ml), followed by heating under reflux for 3 hours. The reaction solution was then distilled off under reduced pressure to yield 4-hydroxy-3,5-di-tert-butylbenzoyl chloride.

5,6-Diamino-3-methyl-1-phenyluracil (0.24 g, 1 mM) prepared by the procedure described in Reference Example 1 was dissolved in 15 ml of chloroform and 1 ml of pyridine was added. To the resulting solution was added dropwise a solution of 4-hydroxy-3,5-di-tert-butylbenzoyl chloride (0.4 g, 1.5 mM) in chloroform under cooling at 0° C. Subsequently, the reaction mixture was brought gradually to room temperature and heated under reflux for 2 hours. The solvent was then distilled off under reduced pressure and the residue was washed with hexane. The residue was purified by a short column chromatograph, washed with ether and dried to yield a product as a white crystal. The product gave the following $^1$H-NMR and mass analysis spectra to be identified as the desired compound 6-amino-5-(3,5-di-tert-butyl-4-hydroxyphenyl)carboxyamido-3-methyl-1-phenyluracil (yield: 0.3 g, or 79% based on 5,6-diamino-3-methyl-1-phenyluracil).

$^1$H-NMR(DMSO-$d_6$) δ ppm; 1.42(18H,s; 2×t-Bu), 3.15 (3H,s; N—CH$_3$), 5.90(2H,brs; —NH$_2$), 7.33–7.75(8H,m; —C$_6$H$_2$—+N—C$_6$H$_5$), 8.79(1H,brs; —NH—CO—)

Mass (m/z): 464(M$^+$)

EXAMPLE 2

6-Amino-5-(3,5-di-tert-butyl-4-hydroxyphenyl) carboxyamido-1-(4-fluorophenyl)-3-methyluracil N-Methyl-N'-(4-fluorophenyl)urea was prepared preliminarily from 4-fluorophenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-3-methyl-1-(4-fluorophenyl)uracil and then reduced with hydrogen gas to prepare 5,6-diamino-1-(4-fluorophenyl)-3-methyluracil.

The procedure of Example 1 was repeated except that 5,6-diamino-1-(4-fluorophenyl)-3-methyluracil rather than 5,6-diamino-3-methyl-1-phenyluracil was reacted with 4-hydroxy-3,5-di-tert-butylbenzoyl chloride. As a result, a product was obtained as a pale yellow crystal. The product gave the following $^1$H-NMR and mass analysis spectra to be identified as the desired compound 6-amino-5-(3,5-di-tert-butyl-4-hydroxyphenyl)carboxyamido-1-(4-fluorophenyl)-3-methyluracil (yield: 71%).

$^1$H-NMR(CDCl$_3$) δ ppm; 1.41(18H,s; 2×t-Bu), 3.15(3H, s; N—CH$_3$), 6.03(2H,brs; —NH$_2$), 7.37–7.41(4H,m; N—C$_6$H$_4$), 7.73(2H,s; —C$_6$H$_2$—), 8.75(1H,brs; —NH—CO—)

Mass (m/z): 482 (M$^+$)

EXAMPLE 3

6-Amino-5-(3,5-di-tert-butyl-4-hydroxyphenyl)carboxyamido-3-methyl-1-(4-methylphenyl)uracil N-Methyl-N'-(4-methylphenyl)urea was prepared preliminarily from 4-methylphenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-(4-methylphenyl)-3-methyluracil and then reduced with hydrogen gas to prepare 5,6-diamino-1-(4-methylphenyl)-3-methyluracil.

The procedure of Example 1 was repeated except that 5,6-diamino-1-(4-methylphenyl)-3-methyluracil rather than 5,6-diamino-3-methyl-1-phenyluracil was reacted with 4-hydroxy-3,5-di-tert-butylbenzoyl chloride. As a result, a product was obtained as a pale yellow crystal. The product gave the following $^1$H-NMR and mass analysis spectra to be identified as the desired compound 6-amino-5-(3,5-di-tert-butyl-4-hydroxyphenyl)carboxyamido-3-methyl-1-(4-methylphenyl)uracil (yield: 71%).

$^1$H-NMR(CDCl$_3$) δ ppm; 1.46(18H,s; 2×t-Bu), 2.39(3H, s; N—C$_6$H$_4$—CH$_3$), 3.15(3H,s; N—CH$_3$), 5.87(2H,brs; —NH$_2$), 7.29(4H,dd; N—C$_6$H$_4$), 7.73(2H,s; —C$_6$H$_2$—), 8.75(1H,brs; —NH—CO—)

Mass (m/z): 478 (M$^+$)

EXAMPLE 4

6-Amino-5-(3,5-di-tert-butyl-4-hydroxyphenyl)carboxyamido-1-(4-methoxyphenyl)-3-methyluracil N-Methyl-N'-(4-methoxyphenyl)urea was prepared preliminarily from 4-methoxyphenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-(4-methoxyphenyl)-3-methyluracil and then reduced with hydrogen gas to prepare 5,6-diamino-1-(4-methoxyphenyl)-3-methyluracil.

The procedure of Example 1 was repeated except that 5,6-diamino-1-(4-methoxyphenyl)-3-methyluracil rather than 5,6-diamino-3-methyl-1-phenyluracil was reacted with 4-hydroxy-3,5-di-tert-butylbenzoyl chloride. As a result, a product was obtained as a pale yellow crystal. The product gave the following $^1$H-NMR and mass analysis spectra to be identified as the desired compound 6-amino-5-(3,5-di-tert-butyl-4-hydroxyphenyl)carboxyamido-1-(4-methoxyphenyl)-3-methyluracil (yield: 40%).

$^1$H-NMR(CDCl$_3$) δ ppm; 1.47(18H,s; 2×t-Bu), 3.39(3H, s; N—CH$_3$), 3.87(3H,s; O—CH$_3$), 5.33(2H,brs; —NH$_2$), 5.63(1H,s; —OH), 7.16(4H,dd; N—C$_6$H$_4$), 7.72(2H,s; —C$_6$H$_2$—), 7.92(1H,brs; —NH—CO—)

Mass (m/z): 494(M$^+$)

EXAMPLE 5

6-Amino-5-(3,5-di-tert-butyl-4-hydroxyphenyl)carboxyamido-1-phenyl-3-propyluracil N-Propyl-N'-phenylurea was prepared preliminarily from phenyl isocyanate and propylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-phenyl-3-propyluracil and then reduced with hydrogen gas to prepare 5,6-diamino-1-phenyl-3-propyluracil.

The procedure of Example 1 was repeated except that 5,6-diamino-1-phenyl-3-propyluracil rather than 5,6-diamino-3-methyl-1-phenyluracil was reacted with 4-hydroxy-3,5-di-tert-butylbenzoyl chloride. As a result, a product was obtained as a pale yellow crystal. The product gave the following $^1$H-NMR and mass analysis spectra to be identified as the desired compound 6-amino-5-(3,5-di-tert-butyl-4-hydroxyphenyl)carboxyamido-1-phenyl-3-propyluracil (yield: 86%).

$^1$H-NMR(DMSO-d$_6$) δ ppm; 0.85(3H,t; —CH$_2$—CH$_2$—CH$_3$), 1.42(18H,s; 2×t-Bu), 1.55(2H,m; —CH$_2$—CH$_2$—CH$_3$), 3.73(2H,m; —CH$_2$—CH$_2$—CH$_3$), 5.88(2H,s; —NH$_2$), 7.33–7.74(7H,m; N—C$_6$H$_5$+—C$_6$H$_2$—), 8.79(1H, brs; —NH—CO—)

Mass (m/z): 492(M$^+$)

EXAMPLE 6

6-Amino-3-benzyl-5-(3,5-di-tert-butyl-4-hydroxyphenyl)carboxyamido-1-phenyluracil N-Benzyl-N'-phenylurea was prepared preliminarily from phenyl isocyanate and benzylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-3-benzyl-1-phenyluracil and then reduced with hydrogen gas to prepare 3-benzyl-5,6-diamino-1-phenyluracil.

The procedure of Example 1 was repeated except that 3-benzyl-5,6-diamino-1-phenyluracil rather than 5,6-diamino-3-methyl-1-phenyluracil was reacted with 4-hydroxy-3,5-di-tert-butylbenzoyl chloride. As a result, a product was obtained as a pale yellow crystal. The product gave the following $^1$H-NMR and mass analysis spectra to be identified as the desired compound 6-amino-3-benzyl-5-(3,5-di-tert-butyl-4-hydroxyphenyl)carboxyamido-1-phenyluracil (yield: 99%).

$^1$H-NMR(DMSO-d$_6$) δ ppm; 1.41(18H,s; 2×t-Bu), 4.97 (2H,s; —CH$_2$—C$_6$H$_5$), 6.01(2H,s; —NH$_2$), 7.29–7.75(13H, m; —CH$_2$—C$_6$H$_5$+—C$_6$H$_2$—+N—C$_6$H$_5$), 8.84(1H,brs; —NH—CO—)

Mass (m/z): 540(M$^+$)

EXAMPLE 7

6-Amino-5-(3,5-diacetoxyphenyl)carboxyamido-3-methyl-1-phenyluracil 3,5-Dihydroxybenzoic acid (7.2 g, 50 mM) was dissolved in 11 ml of acetic anhydride. To the resulting solution were added 5 drops of sulfuric acid, followed by stirring at room temperature for 20 minutes. Subsequently, 10 g of ice was added and 12 ml of 1N hydrochloric acid was then added. After sonication, a precipitated crystal was recovered by filtration. Washing the crystal with toluene gave 3,5-diacetoxybenzoic acid (10.23 g). The obtained 3,5-diacetoxybenzoic acid (2.38 g, 10 mM) was dissolved in 5 ml of SOCl$_2$ and the solution was heated under reflux at 80° C. for 1 hour. The solvent SOCl$_2$ was distilled off under reduced pressure to yield 3,5-diacetoxybenzoyl chloride (2.44 g).

5,6-Diamino-3-methyl-1-phenyluracil (0.92 g, 4 mM) and triethylamine (2 ml) were added to 5 ml of dichloromethane. To the resulting solution was added dropwise a solution of 3,5-diacetoxybenzoyl chloride (1.02 g, 4 mM) in dichloromethane. The reaction mixture was brought gradually to room temperature and heated under reflux for 2 hours. After being left to cool, the reaction mixture was washed with 40 ml of 1N hydrocholric acid. A separated dichloromethane layer was distilled off under reduced pressure to yield a crystal. The crystal was washed with a small amount of ether and a product was obtained as a white crystal (1.0 g). The product gave the following $^1$H-NMR and mass analysis spectra to be identified as the desired compound 6-amino-5-(3,5-diacetoxyphenyl)carboxyamido-3-methyl-1-phenyluracil.

$^1$H-NMR(CDCl$_3$) δ ppm; 2.31(6H,s; 2×—CO—CH$_3$), 3.39(3H,s; N—CH$_3$), 5.29(2H,brs; —NH$_2$), 7.10–7.16(8H, m; N—C$_6$H$_5$+—C$_6$H$_3$—), 8.01(1H,brs; —NH—CO—)

Mass (m/z): 452(M$^+$)

EXAMPLE 8

6-Amino-5-(3,5-diacetoxyphenyl)carboxyamido-1-(4-fluorophenyl)-3-methyluracil

The procedure of Example 7 was repeated except that 5,6-diamino-1-(4-fluorophenyl)-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-5-(3,5-diacetoxyphenyl)carboxyamido-1-(4-fluorophenyl)-3-methyluracil (yield: 77%).

$^1$H-NMR(DMSO-d$_6$) δ ppm; 2.36(6H,s; 2×—CO—CH$_3$), 3.14(3H,s; N—CH$_3$), 6.26(2H,s; —NH$_2$), 7.20–7.66 (7H,m; N—C$_6$H$_4$+—C$_6$H$_3$—), 9.06(1H,brs; —NH—CO—)

Mass (m/z): 470(M$^+$)

EXAMPLE 9

6-Amino-5-(3,5-diacetoxyphenyl)carboxyamido-3-methyl-1-(4-methylphenyl)uracil

The procedure of Example 7 was repeated except that 5,6-diamino-3-methyl-1-(4-methylphenyl)uracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-5-(3,5-diacetoxyphenyl)carboxyamido-3-methyl-1-(4-methylphenyl)uracil (yield: 75%).

$^1$H-NMR(DMSO-d$_6$) δ ppm; 2.17(3H,s; N—C$_6$H$_4$—CH$_3$), 2.35(6H,s; 2×—CO—CH$_3$), 3.15(3H,s; N—CH$_3$), 6.26(2H,s; —NH$_2$), 7.20–7.70(7H,m; N—C$_6$H$_4$+—C$_6$H$_3$—), 9.02(1H,brs; —NH—CO—)

Mass (m/z): 466 (M$^+$)

EXAMPLE 10

6-Amino-5-(3,5-diacetoxyphenyl)carboxyamido-1-(4-methoxyphenyl)-3-methyluracil

The procedure of Example 7 was repeated except that 5,6-diamino-1-(4-methoxyphenyl)-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-5-(3,5-diacetoxyphenyl)carboxyamido-1-(4-methoxyphenyl)-3-methyluracil (yield: 81%).

$^1$H-NMR(DMSO-d$_6$) δ ppm; 2.36(6H,s; 2×—CO—CH$_3$), 3.14(3H,s; N—CH$_3$), 3.88(3H,s; —O—CH$_3$), 6.25 (2H,s; —NH$_2$), 7.15–7.65(7H,m; N—C$_6$H$_4$+—C$_6$H$_3$—), 9.05(1H,brs; —NH—CO—)

Mass (m/z): 482(M$^+$)

EXAMPLE 11

6-Amino-5-(3,5-diacetoxyphenyl)carboxyamido-1-phenyl-3-propyluracil

The procedure of Example 7 was repeated except that 5,6-diamino-1-phenyl-3-propyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-5-(3,5-diacetoxyphenyl)carboxyamido-1-phenyl-3-propyluracil (yield: 96%).

$^1$H-NMR(DMSO-d$_6$) δ ppm; 0.85(3H,t; —CH$_2$—CH$_2$—CH$_3$), 1.53(2H,m; —CH$_2$—CH$_2$—CH$_3$), 2.31(6H,s; 2×—CO—CH$_3$), 3.72(2H,m; —CH$_2$—CH$_2$—CH$_3$), 6.14 (2H,s; —NH$_2$), 7.20–7.66(8H,m; N—C$_6$H$_5$+—C$_6$H$_3$—), 9.07(1H,brs; —NH—CO—)

Mass (m/z): 480(M$^+$)

EXAMPLE 12

6-Amino-3-benzyl-5-(3,5-diacetoxyphenyl)carboxyamido-1-phenyluracil

The procedure of Example 7 was repeated except that 3-benzyl-5,6-diamino-1-phenyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-3-benzyl-5-(3,5-diacetoxyphenyl)carboxyamido-1-phenyluracil (yield: 83%).

$^1$H-NMR(DMSO-d$_6$) δ ppm; 2.30(6H,s; 2×—CO—CH$_3$), 4.96(2H,s; —CH$_2$—C$_6$H$_5$), 6.26(2H,s; —NH$_2$), 7.24–7.66(13H,m; N—C$_6$H$_5$+—C$_6$H$_3$—+—CH$_2$—C$_6$H$_5$), 9.11(1H,s; —NH—CO—)

Mass (m/z): 528 (M$^+$)

EXAMPLE 13

6-Amino-5-(3,5-dimethoxyphenyl)carboxyamido-3-methyl-1-phenyluracil 3,5-Dimethoxybenzoyl chloride was prepared from 3,5-dimethoxybenzoic acid and SOCl$_2$ by the same procedure as in Example 1. The procedure of Example 7 was repeated except that 3,5-dimethoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-5-(3,5-dimethoxyphenyl)carboxyamido-3-methyl-1-phenyluracil (yield: 35%).

$^1$H-NMR(CDCl$_3$) δ ppm; 3.38(3H,s; N—CH$_3$), 3.84(6H, s; 2×—O—CH$_3$), 5.30(2H,brs; —NH$_2$), 7.00–7.60(8H,m; N—C$_6$H$_5$+—C$_6$H$_3$—), 8.01(1H,brs; —NH—CO—)

Mass (m/z): 396 (M$^+$)

EXAMPLE 14

6-Amino-5-(3,5-dihydroxyphenyl)carboxyamido-3-methyl-1-phenyluracil

6-Amino-5-(3,5-diacetoxyphenyl)carboxyamido-3-methyl-1-phenyluracil (1.45 g, 3.2 mM) as prepared in Example 7 was dissolved in 10 ml of acetone and 15 ml of aqueous ammonia was added under cooling with ice. The reaction mixture was then stirred overnight (approximately 10 hours) at room temperature. The solvent was distilled off from the reaction mixture under reduced pressure and the obtained residue was dissolved in ethanol. By the addition of chloroform, a product was obtained as a white crystal (1.2 g). The product gave the following $^1$H-NMR and mass analysis spectra to be identified as the desired compound 6-amino-5-(3,5-dihydroxyphenyl)-carboxyamido-3-methyl-1-phenyluracil (yield: 100% based on the compound prepared in Example 7).

$^1$H-NMR(DMSO-d$_6$) δ ppm; 3.14(3H,s; N—CH$_3$), 6.37 (1H,m; p-position of —C$_6$H$_3$—), 6.83(2H,m; o-position of —C$_6$H$_3$—), 7.30–7.60(5H,m; N—C$_6$H$_5$), 8.69(1H,s; —NH—CO—), 9.42(2H,s; 2×—OH)

Mass (m/z): 368 (M$^+$)

EXAMPLE 15

5-(3,5-Diacetoxyphenyl)carboxyamido-3-methyl-6-methylamino-1-phenyluracil

The procedure of Example 7 was repeated except that 5-amino-3-methyl-6-methylamino-1-phenyluracil (the compound prepared in Reference Example 2) rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 5-(3,5-diacetoxyphenyl)carboxyamido-3-methyl-6-methylamino-1-phenyluracil (yield: 82%).

$^1$H-NMR(DMSO-d$_6$) δ ppm; 2.29(6H,s; 2×—CO—CH$_3$), 2.62(3H,d; NH—CH$_3$), 3.15(3H,s; N—CH$_3$), 3.33 (1H,m; NH—CH$_3$), 7.20–7.62(8H,m; N—C$_6$H$_5$+—C$_6$H$_3$—), 9.30(1H,brs; —NH—CO—)

Mass (m/z): 466 (M$^+$)

EXAMPLE 16

5-(3,5-Diacetoxyphenyl)carboxyamido-6-methylamino-1-phenyl-3-propyluracil

N-Propyl-N'-phenylurea was prepared preliminarily from phenyl isocyanate and propylamine by the same procedure as in Reference Example 1. The urea compound as the starting material was reacted with cyanoacetic acid to form a uracil ring. Subsequently, 6-amino-1-phenyl-3-propyluracil was treated as in Reference Example 2 so that the substituent amino group at the 6-position was converted to a methylamino group to yield 6-methylamino-1-phenyl-3-propyluracil. Using sodium nitrite a nitroso group was introduced into the 5-position of the uracil ring and then reduced with hydrogen gas to prepare 5-amino-6-methylamino-1-phenyl-3-propyluracil.

The procedure of Example 7 was repeated except that 5-amino-6-methylamino-1-phenyl-3-propyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 5-(3,5-diacetoxyphenyl)carboxyamido-6-methylamino-1-phenyl-3-propyluracil (yield: 72%).

$^1$H-NMR(CDCl$_3$) δ ppm; 0.93(3H,t; —CH$_2$—CH$_2$—CH$_3$), 1.67(2H,m; —CH$_2$—CH$_2$—CH$_3$), 2.30(6H,s; 2×—CO—CH$_3$), 2.70(3H,d; NH—CH$_3$), 3.89(2H,m; —CH$_2$—CH$_2$—CH$_3$), 4.31(1H,m; NH—CH$_3$), 7.11–7.57(8H, m; N—C$_6$H$_5$+—C$_6$H$_3$—), 7.64(1H,s; —NH—CO—)

Mass (m/z): 494 (M$^+$)

EXAMPLE 17

5-(3,5-Diacetoxyphenyl)carboxyamido-6-dimethylamino-1-(4-fluorophenyl)-3-methyluracil N-Methyl-N'-(4-fluorophenyl)urea was prepared preliminarily from 4-fluorophenyl isocyanate and methylamine by the same procedure as in Reference Example 1. The urea compound as the starting material was reacted with cyanoacetic acid to form a uracil ring. Subsequently, 6-amino-1-(4-fluorophenyl)-3-methyluracil was treated as in Reference Example 2 so that the substituent amino group at the 6-position was converted to a dimethylamino group to yield 6-dimethylamino-1-(4-fluorophenyl)-3-methyluracil. Using a mixed acid that had been prepared with sulfuric acid and nitric acid, a nitro group was introduced into the 5-position of the uracil ring and then reduced with hydrogen gas to prepare 5-amino-6-dimethylamino-1-(4-fluorophenyl)-3-methyluracil.

The procedure of Example 7 was repeated except that 5-amino-6-dimethylamino-1-(4-fluorophenyl)-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 5-(3,5-diacetoxyphenyl)carboxyamido-6-dimethylamino-1-(4-fluorophenyl)-3-methyluracil (yield: 44%).

$^1$H-NMR(DMSO-d$_6$) δ ppm; 2.31(6H,s; 2×—CO—CH$_3$), 2.37(6H,s; N(CH$_3$)$_2$), 3.19(3H,s; N—CH$_3$), 7.26–7.64 (7H,m; N—C$_6$H$_4$—+—C$_6$H$_3$—), 9.52(1H,brs; —NH—CO—)

Mass (m/z): 498 (M$^+$)

EXAMPLE 18

6-Amino-5-(3,5-diacetoxy-4-methylphenyl)carboxyamido-3-methyl-1-phenyluracil

The hydroxyl groups in 3,5-dihydroxy-4-methylbenzoic acid were acetylated by the same procedure as in Example 7 to yield 3,5-diacetoxy-4-methylbenzoic acid. The obtained 3,5-diacetoxy-4-methylbenzoic acid was reacted with $SOCl_2$ to prepare 3,5-diacetoxy-4-methylbenzoyl chloride.

The procedure of Example 7 was repeated except that 3,5-diacetoxy-4-methylbenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-5-(3,5-diacetoxy-4-methylphenyl)carboxyamido-3-methyl-1-phenyluracil (yield: 45%).

$^1$H-NMR(CDCl$_3$) δ ppm; 1.99(3H,s; —C$_6$H$_4$—CH$_3$), 2.27(6H,s; 2×—CO—CH$_3$), 3.28(3H,s; N—CH$_3$), 5.19(2H, brs; —NH$_2$), 7.20-7.60(7H,m; N—C$_6$H$_5$+—C$_6$H$_2$—), 7.98 (1H,brs; —NH—CO—)

Mass (m/z): 466 (M$^+$)

EXAMPLE 19

6-Amino-1-(4-chlorophenyl)-5-(3,5-diacetoxyphenyl)carboxyamido-3-methyluracil

N-Methyl-N'-(4-chlorophenyl)urea was prepared preliminarily from 4-chlorophenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-(4-chlorophenyl)-3-methyluracil and then reduced with hydrogen gas to prepare 1-(4-chlorophenyl)-5,6-diamino-3-methyluracil.

The procedure of Example 7 was repeated except that 1-(4-chlorophenyl)-5,6-diamino-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-1-(4-chlorophenyl)-5-(3,5-diacetoxyphenyl)carboxyamido-3-methyluracil (yield: 85%).

$^1$H-NMR(DMSO-d$_6$) δ ppm; 2.36(6H,s; 2×—CO—CH$_3$), 3.15(3H,s; N—CH$_3$), 6.26(2H,s; —NH$_2$), 7.20-7.70 (7H,m; N—C$_6$H$_4$—+—C$_6$H$_3$—), 9.06(1H,brs; —NH—CO—)

Mass (m/z): 487(M$^+$)

EXAMPLE 20

6-Amino-1-(2-chlorophenyl)-5-(3,5-diacetoxyphenyl)carboxyamido-3-methyluracil

N-Methyl-N'-(2-chlorophenyl)urea was prepared preliminarily from 2-chlorophenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-(2-chlorophenyl)-3-methyluracil and then reduced with hydrogen gas to prepare 1-(2-chlorophenyl)-5,6-diamino-3-methyluracil.

The procedure of Example 7 was repeated except that 1-(2-chlorophenyl)-5,6-diamino-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-1-(2-chlorophenyl)-5-(3,5-diacetoxyphenyl)carboxyamido-3-methyluracil (yield: 74%).

$^1$H-NMR(DMSO-d$_6$) δ ppm; 2.35(6H,s; 2×—CO—CH$_3$), 3.14(3H,s; N—CH$_3$), 6.26(2H,s; —NH$_2$), 7.25-7.66 (7H,m; N—C$_6$H$_4$—+—C$_6$H$_3$—), 9.56(1H,brs; —NH—CO—)

Mass (m/z): 487(M$^+$)

EXAMPLE 21

6-Amino-1-(3-chlorophenyl)-5-(3,5-diacetoxyphenyl)carboxyamido-3-methyluracil

N-Methyl-N'-(3-chlorophenyl)urea was prepared preliminarily from 3-chlorophenyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-1-(3-chlorophenyl)-3-methyluracil and then reduced with hydrogen gas to prepare 1-(3-chlorophenyl)-5,6-diamino-3-methyluracil.

The procedure of Example 7 was repeated except that 1-(3-chlorophenyl)-5,6-diamino-3-methyluracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-1-(3-chlorophenyl)-5-(3,5-diacetoxyphenyl)carboxyamido-3-methyluracil (yield: 76%).

$^1$H-NMR(DMSO-d$_6$) δ ppm; 2.36(6H,s; 2×—CO—CH$_3$), 3.16(3H,s; N—CH$_3$), 6.23(2H,s; —NH$_2$), 7.10-7.66 (7H,m; N—C$_6$H$_4$—+—C$_6$H$_3$—), 9.54(1H,brs; —NH—CO—)

Mass (m/z): 487(M$^+$)

EXAMPLE 22

6-Amino-3-methyl-1-phenyl-5-(3,4,5-triacetoxyphenyl)carboxyamidouracil

The hydroxyl groups in 3,4,5-trihydroxybenzoic acid were acetylated by the same procedure as in Example 7 to yield 3,4,5-triacetoxybenzoic acid. The obtained 3,4,5-triacetoxybenzoic acid was reacted with $SOCl_2$ to prepare 3,4,5-triacetoxybenzoyl chloride.

The procedure of Example 7 was repeated except that 3,4,5-triacetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-3-methyl-1-phenyl-5-(3,4,5-triacetoxyphenyl)carboxyamidouracil (yield: 36%).

$^1$H-NMR(CDCl$_3$) δ ppm; 2.30(6H,s; 2×—CO—CH$_3$ (m-positions)), 2.31(3H,s; —CO—CH$_3$ (p-position)), 3.38 (3H,s; N—CH$_3$), 5.25(2H,brs; —NH$_2$), 7.10-7.70(7H,m; N—C$_6$H$_5$+—C$_6$H$_2$—), 7.98(1H,brs; —NH—CO—)

Mass (m/z): 510 (M$^+$)

EXAMPLE 23

6-Amino-1-(4-fluorophenyl)-3-methyl-5-(3,4,5-triacetoxyphenyl)carboxyamidouracil The procedure of Example 22 was repeated except that 5,6-diamino-1-(4-fluorophenyl)-3-methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-(4-fluorophenyl)-3-methyl-5-(3,4,5-triacetoxyphenyl)carboxyamidouracil (yield: 51%).

$^1$H-NMR(CDCl$_3$) δ ppm; 2.28(6H,s; 2×—CO—CH$_3$ (m-positions)), 2.30(3H,s; —CO—CH$_3$ (p-position)), 3.38 (3H,s; N—CH$_3$), 5.27(2H,brs; —NH$_2$), 7.10–7.70(6H,m; N—C$_6$H$_4$—+—C$_6$H$_2$—), 7.99(1H,brs; —NH—CO—)

Mass (m/z): 528 (M$^+$)

EXAMPLE 24

6-Amino-1-(4-methoxyphenyl)-3-methyl-5-(3,4,5-triacetoxyphenyl)carboxyamidouracil The procedure of Example 22 was repeated except that 5,6-diamino-1-(4-methoxyphenyl)-3-methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-(4-methoxyphenyl)-3-methyl-5-(3,4,5-triacetoxyphenyl)carboxyamidouracil (yield: 43%).

$^1$H-NMR(CDCl$_3$) δ ppm; 2.28(6H,s; 2×—CO—CH$_3$ (m-positions)), 2.30(3H,s; —CO—CH$_3$ (p-position)), 3.37 (3H,s; N—CH$_3$), 3.85(3H,s; —O—CH$_3$), 5.25(2H,brs; —NH$_2$), 7.10–7.60(6H,m; N—C$_6$H$_4$—+—C$_6$H$_2$—), 8.01(1H, brs; —NH—CO—)

Mass (m/z): 540 (M$^+$)

EXAMPLE 25

6-Amino-3-methyl-1-(4-methylphenyl)-5-(3,4,5-triacetoxyphenyl)carboxyamidouracil The procedure of Example 22 was repeated except that 5,6-diamino-3-methyl-1-(4-methylphenyl)uracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-3-methyl-1-(4-methylphenyl)-5-(3,4,5-triacetoxyphenyl)carboxyamidouracil (yield: 51%).

$^1$H-NMR(CDCl$_3$) δ ppm; 2.18(3H,s; —C$_6$H$_4$—CH$_3$), 2.28(6H,s; 2×—CO—CH$_3$ (m-positions)), 2.30(3H,s; —CO—CH$_3$ (p-position)), 3.38(3H,s; N—CH$_3$), 5.24(2H, brs; —NH$_2$), 7.10–7.60(6H,m; N—C$_6$H$_4$—+—C$_6$H$_2$—), 8.02(1H,brs; —NH—CO—) Mass (m/z): 524 (M$^+$)

EXAMPLE 26

6-Amino-1-phenyl-3-propyl-5-(3,4,5-triacetoxyphenyl)carboxyamidouracil

The procedure of Example 22 was repeated except that 5,6-diamino-1-phenyl-3-propyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-phenyl-3-propyl-5-(3,4,5-triacetoxyphenyl)carboxyamidouracil (yield: 55%).

$^1$H-NMR(DMSO-d$_6$) δ ppm; 0.88(3H,t; —CH$_2$—CH$_2$—CH$_3$), 1.54(2H,m; —CH$_2$—CH$_2$—CH$_3$), 2.30(6H,s; 2×—CO—CH$_3$ (m-positions)), 2.31(3H,s; —CO—CH$_3$ (p-position)), 3.70(2H,m; —CH$_2$—CH$_2$—CH$_3$), 6.15(2H,s; —NH$_2$), 7.20–7.70(7H,m; N—C$_6$H$_5$+—C$_6$H$_2$—), 9.07(1H, brs; —NH—CO—)

Mass (m/z): 528 (M$^+$)

EXAMPLE 27

6-Amino-3-benzyl-1-phenyl-5-(3,4,5-triacetoxyphenyl)carboxyamidouracil

The procedure of Example 22 was repeated except that 3-benzyl-5,6-diamino-1-phenyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-3-benzyl-1-phenyl-5-(3,4,5-triacetoxyphenyl)carboxyamidouracil (yield: 53%).

$^1$H-NMR(DMSO-d$_6$) δ ppm; 2.30(6H,s; 2×—CO—CH$_3$ (m-positions)), 2.31(3H,s; —CO—CH$_3$ (p-position)), 5.00 (2H,s; —CH$_2$—C$_6$H$_5$), 6.24(2H,s; —NH$_2$), 7.20–7.70(12H, m; N—C$_6$H$_5$+—C$_6$H$_2$—+—CH$_2$—C$_6$H$_5$), 9.07(1H,brs; —NH—CO—)

Mass (m/z): 586(M$^+$)

EXAMPLE 28

3-Methyl-6-methylamino-1-phenyl-5-(3,4,5-triacetoxyphenyl)carboxyamidouracil

The procedure of Example 22 was repeated except that 5-amino-3-methyl-6-methylamino-1-phenyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 3-methyl-6-methylamino-1-phenyl-5-(3,4,5-triacetoxyphenyl)carboxyamidouracil (yield: 42%).

$^1$H-NMR(DMSO-d$_6$) δ ppm; 2.30(6H,s; 2×—CO—CH$_3$ (m-positions)), 2.31(3H,s; —CO—CH$_3$ (p-position)), 2.62 (3H,d; —NH—CH$_3$), 3.14(3H,s; N—CH$_3$), 3.33(1H,m; —NH—CH$_3$), 7.10–7.60(7H,m; N—C$_6$H$_5$+—C$_6$H$_2$—), 8.07 (1H,brs; —NH—CO—)

Mass (m/z): 524(M$^+$)

EXAMPLE 29

6-Amino-3-methyl-1-phenyl-5-(3,4,5-trihydroxyphenyl)-carboxyamidouracil

6-Amino-3-methyl-1-phenyl-5-(3,4,5-triacetoxyphenyl) carboxyamidouracil (0.12 g) as prepared in Example 22 was deacetylated by the same procedure as in Example 14 to yield a product as a white crystal (0.07 g). The product gave the following $^1$H-NMR and mass analysis spectra to be identified as the desired compound 6-amino-3-methyl-1-phenyl-5-(3,4,5-trihydroxyphenyl)carboxyamidouracil (yield: 75%).

$^1$H-NMR(DMSO-d$_6$) δ ppm; 3.15(3H,s; N—CH$_3$), 5.83 (2H,s; —NH$_2$), 6.97(2H,s; —C$_6$H$_2$—), 7.33–7.60(5H,m; N—C$_6$H$_5$), 8.53(1H,brs; —NH—CO—)

Mass (m/z): 384 (M$^+$)

EXAMPLE 30

6-Dimethylamino-1-(4-fluorophenyl)-3-methyl-5-(3,4,5-triacetoxyphenyl)carboxyamidouracil The procedure of Example 22 was repeated except that 5-amino-6-dimethylamino-1-(4-fluorophenyl)-3- methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-dimethylamino-1-(4-fluorophenyl)-3-methyl-5-(3,4,5-triacetoxyphenyl)carboxyamidouracil (yield: 53%).

$^1$H-NMR(DMSO-d$_6$) δ ppm; 2.28(6H,s; 2×—CO—CH$_3$ (m-positions)), 2.30(3H,s; —CO—CH$_3$ (p-position)), 2.35 (6H,s; N(CH$_3$)$_2$), 3.22(3H,s; N—CH$_3$), 5.22(2H,brs; —NH$_2$) 7.10–7.60(6H,m; N—C$_6$H$_4$—+—C$_6$H$_2$—), 9.09(1H, brs; —NH—CO—)

Mass (m/z): 556 (M$^+$)

EXAMPLE 31

6-Amino-1-(4-chlorophenyl)-3-methyl-5-(3,4,5-triacetoxyphenyl)carboxyamidouracil The procedure of Example 22 was repeated except that 1-(4-chlorophenyl)-5,6-diamino-3-methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-(4-chlorophenyl)-3-methyl-5-(3,4,5-triacetoxyphenyl)carboxyamidouracil (yield: 61%).

$^1$H-NMR(CDCl$_3$) δ ppm; 2.28(6H,s; 2×—CO—CH$_3$ (m-positions)), 2.30(3H,s; —CO—CH$_3$ (p-position)), 3.34 (3H,s; N—CH$_3$), 5.26(2H,brs; —NH$_2$), 7.10–7.70(6H,m; N—C$_6$H$_4$—+—C$_6$H$_2$—), 9.04(1H,brs; —NH—CO—)

Mass (m/z): 545 (M$^+$)

EXAMPLE 32

6-Amino-1-(2-chlorophenyl)-3-methyl-5-(3,4,5-triacetoxyphenyl)carboxyamidouracil The procedure of Example 22 was repeated except that 1-(2-chlorophenyl)-5,6-diamino-3-methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-(2-chlorophenyl)-3-methyl-5-(3,4,5-triacetoxyphenyl)carboxyamidouracil (yield: 51%).

$^1$H-NMR(CDCl$_3$) δ ppm; 2.28(6H,s; 2×—CO—CH$_3$ (m-positions)), 2.31(3H,s; —CO—CH$_3$ (p-position)), 3.38 (3H,s; N—CH$_3$), 5.26(2H,brs; —NH$_2$), 7.10–7.60(7H,m; N—C$_6$H$_4$—+—C$_6$H$_2$—), 9.59(1H,brs; —NH—CO—)

Mass (m/z): 545 (M$^+$)

EXAMPLE 33

6-Amino-1-(3-chlorophenyl)-3-methyl-5-(3,4,5-triacetoxyphenyl)carboxyamidouracil The procedure of Example 22 was repeated except that 1-(3-chlorophenyl)-5,6-diamino-3-methyluracil rather than 5,6-diamino-3-methyl-1-phenyluracil was reacted with 3,4,5-triacetoxybenzoyl chloride. As a result, a product was obtained as a white crystal. The product gave the following $^1$H-NMR and mass analysis spectra to be identified as the desired compound 6-amino-1-(3-chlorophenyl)-3-methyl-5-(3,4,5-triacetoxyphenyl)carboxyamidouracil (yield: 50%).

$^1$H-NMR(CDCl$_3$) δ ppm; 2.27(6H,s; 2×—CO—CH$_3$ (m-positions)), 2.30(3H,s; —CO—CH$_3$ (p-position)), 3.39 (3H,s; N—CH$_3$), 5.27(2H,brs; —NH$_2$), 7.10–7.70(7H,m; N—C$_6$H$_4$—+—C$_6$H$_2$—), 9.55(1H,brs; —NH—CO—)

Mass (m/z): 545 (M$^+$)

EXAMPLE 34

6-Amino-5-(3,4-diacetoxyphenyl)carboxyamido-3-methyl-1-phenyluracil

The hydroxyl groups in 3,4-dihydroxybenzoic acid were acetylated by the same procedure as in Example 7 to yield 3,4-diacetoxybenzoic acid. The obtained 3,4-diacetoxybenzoic acid was reacted with SOCl$_2$ to prepare 3,4-diacetoxybenzoyl chloride.

The procedure of Example 7 was repeated except that 3,4-diacetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-5-(3,4-diacetoxyphenyl)carboxyamido-3-methyl-1-phenyluracil (yield: 36%).

$^1$H-NMR(CDCl$_3$) δ ppm; 2.31(6H,m; 2×—CO—CH$_3$), 3.39(3H,s; N—CH$_3$), 5.29(2H,brs; —NH$_2$), 7.30–7.80(8H, m; N—C$_6$H$_5$+—C$_6$H$_3$—), 8.02(1H,brs; —NH—CO—)

Mass (m/z): 452 (M$^+$)

EXAMPLE 35

6-Amino-5-(3,4-diacetoxyphenyl)carboxyamido-1-(4-fluorophenyl)-3-methyluracil

The procedure of Example 34 was repeated except that 5,6-diamino-1-(4-fluorophenyl)-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-5-(3,4-diacetoxyphenyl)carboxyamido-1-(4-fluorophenyl)-3-methyluracil (yield: 64%).

$^1$H-NMR(CDCl$_3$) δ ppm; 2.30(6H,m; 2×—CO—CH$_3$), 3.40(3H,s; N—CH$_3$), 5.26(2H,s; —NH$_2$), 7.20–7.66(7H,m; N—C$_6$H$_4$—+—C$_6$H$_3$—), 8.06(1H,brs; —NH—CO—)

Mass (m/z): 470(M$^+$)

EXAMPLE 36

6-Amino-5-(3,4-diacetoxyphenyl)carboxyamido-3-methyl-1-(4-methylphenyl)uracil

The procedure of Example 34 was repeated except that 5,6-diamino-3-methyl-1-(4-methylphenyl)uracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-5-(3,4-diacetoxyphenyl)carboxyamido-3-methyl-1-(4-methylphenyl)uracil (yield: 71%).

$^1$H-NMR(CDCl$_3$) δ ppm; 2.30(6H,m; 2×—CO—CH$_3$), 2.39(3H,s; N—C$_6$H$_4$—CH$_3$), 3.38(3H,s; N—CH$_3$), 5.26 (2H,s; —NH$_2$), 7.20–7.70(7H,m; N—C$_6$H$_4$—+—C$_6$H$_3$—), 8.00(1H,brs; —NH—CO—)

Mass (m/z): 466 (M$^+$)

EXAMPLE 37

6-Amino-5-(3,4-diacetoxyphenyl)carboxyamido-1-(4-methoxyphenyl)-3-methyluracil

The procedure of Example 34 was repeated except that 5,6-diamino-1-(4-methoxyphenyl)-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-5-(3,4-diacetoxyphenyl)carboxyamido-1-(4-methoxyphenyl)-3-methyluracil (yield: 59%).

$^1$H-NMR(CDCl$_3$) δ ppm; 2.30(6H,m; 2×—CO—CH$_3$), 3.40(3H,s; N—CH$_3$), 3.88(3H,s; —O—CH$_3$), 5.25(2H,s; —NH$_2$), 7.20–7.70(7H,m; N—C$_6$H$_4$—+—C$_6$H$_3$—), 8.03(1H, brs; —NH—CO—)

Mass (m/z): 482(M$^+$)

EXAMPLE 38

6-Amino-5-(3,4-diacetoxyphenyl)carboxyamido-1-phenyl-3-propyluracil

The procedure of Example 34 was repeated except that 5,6-diamino-1-phenyl-3-propyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-5-(3,4-diacetoxyphenyl)carboxyamido-1-phenyl-3-propyluracil (yield: 72%).

$^1$H-NMR(DMSO-d$_6$) δ ppm; 0.80(3H,t; —CH$_2$—CH$_2$—CH$_3$), 1.53(2H,m; —CH$_2$—CH$_2$—CH$_3$), 2.30(6H,m; 2×—CO—CH$_3$), 3.70(2H,m; —CH$_2$—CH$_2$—CH$_3$), 6.14 (2H,s; —NH$_2$), 7.10–7.60(8H,m; N—C$_6$H$_5$+—C$_6$H$_3$—), 9.03(1H,brs; —NH—CO—)

Mass (m/z): 480(M$^+$)

EXAMPLE 39

6-Amino-3-benzyl-5-(3,4-diacetoxyphenyl)carboxyamido-1-phenyluracil

The procedure of Example 34 was repeated except that 3-benzyl-5,6-diamino-1-phenyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-3-benzyl-5-(3,4-diacetoxyphenyl)carboxyamido-1-phenyluracil (yield: 86%).

$^1$H-NMR(DMSO-d$_6$) δ ppm; 2.30(6H,m; 2×—CO—CH$_3$), 4.91(2H,s; —CH$_2$—C$_6$H$_5$), 6.22(2H,s; —NH$_2$), 7.20–7.70(13H,m; N—C$_6$H$_5$+—C$_6$H$_3$—+—CH$_2$—C$_6$H$_5$), 9.01(1H,s; —NH—CO—)

Mass (m/z): 528 (M$^+$)

EXAMPLE 40

6-Amino-5-(3,4-dihydroxyphenyl)carboxyamido-3-methyl-1-phenyluracil

6-Amino-5-(3,4-diacetoxyphenyl)carboxyamido-3-methyl-1-phenyluracil (1.5 g) as prepared in Example 34 was deacetylated by the same procedure as in Example 14 to yield a product as a white crystal (1.2 g). The product gave the following $^1$H-NMR and mass analysis spectra to be identified as the desired compound 6-amino-5-(3,4-dihydroxyphenyl)carboxyamido-3-methyl-1-phenyluracil (yield: 100% based on the compound prepared in Example 34).

$^1$H-NMR(DMSO-d$_6$) δ ppm; 3.15(3H,s; N—CH$_3$), 6.40 (1H,m; m-position of —C$_6$H$_3$—), 6.88(2H,m; o-position of —C$_6$H$_3$—), 7.20–7.60(5H,m; N—C$_6$H$_5$), 8.74(1H,s; —NH—CO—), 9.38(2H,brs; 2×—OH)

Mass (m/z): 368 (M$^+$)

EXAMPLE 41

5-(3,4-Diacetoxyphenyl)carboxyamido-3-methyl-6-methylamino-1-phenyluracil

The procedure of Example 34 was repeated except that 5-amino-3-methyl-6-methylamino-1-phenyluracil (the compound prepared in Reference Example 2) rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 5-(3,4-diacetoxyphenyl)carboxyamido-3-methyl-6-methylamino-1-phenyluracil (yield: 88%).

$^1$H-NMR(DMSO-d$_6$) δ ppm; 2.30(6H,m; 2×—CO—CH$_3$), 2.62(3H,d; —NH—CH$_3$), 3.19(3H,s; —N—CH$_3$), 3.34(1H,m; —NH—CH$_3$), 7.20–7.72(8H,m; N—C$_6$H$_5$+—C$_6$H$_3$—), 9.10(1H,brs; —NH—CO—)

Mass (m/z): 466 (M$^+$)

EXAMPLE 42

5-(3,4-Diacetoxyphenyl)carboxyamido-6-methylamino-1-phenyl-3-propyluracil

The procedure of Example 34 was repeated except that 5-amino-6-methylamino-1-phenyl-3-propyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 5-(3,4-diacetoxyphenyl)carboxyamido-6-methylamino-1-phenyl-3-propyluracil (yield: 79%).

$^1$H-NMR(CDCl$_3$) δ ppm; 0.90(3H,t; —CH$_2$—CH$_2$—CH$_3$), 1.66(2H,m; —CH$_2$—CH$_2$—CH$_3$), 2.30(6H,m; 2×—CO—CH$_3$), 2.64(3H,d; —NH—CH$_3$), 3.88(2H,m; —CH$_2$—CH$_2$—CH$_3$), 4.31(1H,m; —NH—CH$_3$), 7.10–7.55 (8H,m; N—C$_6$H$_5$+—C$_6$H$_3$—), 7.65(1H, s; —NH—CO—)

Mass (m/z): 494 (M$^+$)

EXAMPLE 43

5-(3,4-Diacetoxyphenyl)carboxyamido-6-dimethylamino-1-(4-fluorophenyl)-3-methyluracil The procedure of Example 34 was repeated except that 5-amino-6-dimethylamino-1-(4-fluorophenyl)-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 5-(3,4-diacetoxyphenyl)carboxyamido-6-dimethylamino-1-(4-fluorophenyl)-3-methyluracil (yield: 52%).

$^1$H-NMR(DMSO-d$_6$) δ ppm; 2.31(6H,m; 2×—CO—CH$_3$), 2.38(6H,s; N(CH$_3$)$_2$), 3.18(3H,s; N—CH$_3$), 7.25–7.64 (7H,m; N—C$_6$H$_4$—+—C$_6$H$_3$—), 9.51(1H,brs; —NH—CO—)

Mass (m/z): 498 (M$^+$)

EXAMPLE 44

6-Amino-1-(4-chlorophenyl)-5-(3,4-diacetoxyphenyl)carboxyamido-3-methyluracil

The procedure of Example 34 was repeated except that 1-(4-chlorophenyl)-5,6-diamino-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-1-(4-chlorophenyl)-5-(3,4-diacetoxyphenyl)carboxyamido-3-methyluracil (yield: 71%).

$^1$H-NMR(DMSO-d$_6$) δ ppm; 2.31(6H,m; 2×—CO—CH$_3$), 3.19(3H,s; N—CH$_3$), 6.01(2H,s; —NH$_2$), 7.30–7.70 (7H,m; N—C$_6$H$_4$—+—C$_6$H$_3$—), 9.50(1H,brs; —NH—CO—)

Mass (m/z): 487(M$^+$)

EXAMPLE 45

6-Amino-1-(2-chlorophenyl)-5-(3,4-diacetoxyphenyl)carboxyamido-3-methyluracil The procedure of Example 34 was repeated except that 1-(2-chlorophenyl)-5,6-diamino-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-1-(2-chlorophenyl)-5-(3,4-diacetoxyphenyl)carboxyamido-3-methyluracil (yield: 41%).

$^1$H-NMR(DMSO-d$_6$) δ ppm; 2.31(6H,m; 2×—CO—CH$_3$), 3.20(3H,s; N—CH$_3$), 5.98(2H,s; —NH$_2$), 7.25–7.70 (7H,m; N—C$_6$H$_4$—+—C$_6$H$_3$—), 10.50(1H,brs; —NH—CO—)

Mass (m/z): 487(M$^+$)

EXAMPLE 46

6-Amino-1-(3-chlorophenyl)-5-(3,4-diacetoxyphenyl)carboxyamido-3-methyluracil The procedure of Example 34 was repeated except that 1-(3-chlorophenyl)-5,6-diamino-3-methyluracil rather than 5,6-diamino-3-methyl-1-phenyluracil was reacted with 3,4-diacetoxybenzoyl chloride. As a result, a product was obtained as a white crystal. The product gave the following $^1$H-NMR and mass analysis spectra to be identified as the desired compound 6-amino-1-(3-chlorophenyl)-5-(3,4-diacetoxyphenyl)carboxyamido-3-methyluracil (yield: 61%).

$^1$H-NMR(DMSO-d$_6$) δ ppm; 2.30(6H,m; 2×—CO—CH$_3$), 3.17(3H,s; N—CH$_3$), 5.89(2H,s; —NH$_2$), 7.20–7.70 (7H,m; N—C$_6$H$_4$—+—C$_6$H$_3$—), 10.51(1H,brs; —NH—CO—)

Mass (m/z): 487(M$^+$)

EXAMPLE 47

5-(4-Acetoxy-3-methoxyphenyl)carboxyamido-6-amino-3-methyl-1-phenyluracil

The hydroxyl group in 4-hydroxy-3-methoxybenzoic acid was acetylated by the same procedure as in Example 7 to yield 4-acetoxy-3-methoxybenzoic acid. The obtained 4-acetoxy-3-methoxybenzoic acid was reacted with SOCl$_2$ to prepare 4-acetoxy-3-methoxybenzoyl chloride.

The procedure of Example 7 was repeated except that 4-acetoxy-3-methoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(4-acetoxy-3-methoxyphenyl)carboxyamido-6-amino-3-methyl-1-phenyluracil (yield: 65%).

$^1$H-NMR(CDCl$_3$) δ ppm; 2.33(3H,s; —CO—CH$_3$), 3.36 (3H,s; N—CH$_3$), 3.87(3H,s; —O—CH$_3$), 5.22(2H,brs; —NH$_2$), 7.10–7.60(8H,m; N—C$_6$H$_5$+—C$_6$H$_3$—), 8.40(1H,brs; —NH—CO—)

Mass (m/z): 424 (M$^+$)

EXAMPLE 48

5-(3-Acetoxy-4-methoxyphenyl)carboxyamido-6-amino-3-methyl-1-phenyluracil

The hydroxyl group in 3-hydroxy-4-methoxybenzoic acid was acetylated by the same procedure as in Example 7 to yield 3-acetoxy-4-methoxybenzoic acid. The obtained 3-acetoxy-4-methoxybenzoic acid was reacted with SOCl$_2$ to prepare 3-acetoxy-4-methoxybenzoyl chloride.

The procedure of Example 7 was repeated except that 3-acetoxy-4-methoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(3-acetoxy-4-methoxyphenyl)carboxyamido-6-amino-3-methyl-1-phenyluracil (yield: 60%).

$^1$H-NMR(CDCl$_3$) δ ppm; 2.33(3H,s; —CO—CH$_3$), 3.36 (3H,s; N—CH$_3$), 3.87(3H,s; —O—CH$_3$), 5.22(2H,brs; —NH$_2$), 7.10–7.60(8H,m; N—C$_6$H$_5$+—C$_6$H$_3$—), 8.40(1H,brs; —NH—CO—)

Mass (m/z): 424 (M$^+$)

EXAMPLE 49

6-Amino-5-(3,4-diacetoxystyryl)carboxyamido-3-methyl-1-phenyluracil

The hydroxyl groups in 3-(3,4-dihydroxyphenyl)-2-propenoic acid (m,p-dihydroxycinnamic acid) were acetylated by the same procedure as in Example 7 to yield 3-(3,4-diacetoxyphenyl)-2-propenoic acid (m,p-acetoxycinnamic acid). The obtained 3-(3,4-diacetoxyphenyl)-2-propenoic acid (m,p-acetoxycinnamic acid) was reacted with SOCl$_2$ to prepare m,p-diacetoxycinnamoyl chloride (3-(3,4-diacetoxyphenyl)-2-propenoic acid chloride).

The procedure of Example 7 was repeated except that m,p-diacetoxycinnamoyl chloride (3-(3,4-diacetoxyphenyl) -2-propenoic acid chloride) rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-5-(3,4-diacetoxystyryl)carboxyamido-3-methyl-1-phenyluracil (yield: 5%).

$^1$H-NMR(CDCl$_3$) δ ppm; 1.61(3H,s; —CO—CH$_3$ (p-position)), 2.30(3H,s; —CO—CH$_3$ (m-position)),3.40 (3H,s; N—CH$_3$), 5.40(2H,brs; —NH$_2$), 6.60(1H,d; —CH=CH—C$_6$H$_3$—), 7.10–7.60(9H,m; N—C$_6$H$_5$+—CH=CH—C$_6$H$_3$—+—CH=CH—C$_6$H$_3$—), 7.72(1H,brs; —NH—CO—)

Mass (m/z): 478 (M$^+$)

EXAMPLE 50

5-(4-Acetoxy-3-methoxystyryl)carboxyamido-6-amino-3-methyl-1-phenyluracil

The hydroxyl group in 3-(4-hydroxy-3-methoxyphenyl)-2-propenoic acid (p-hydroxy-m-methoxycinnamic acid) was acetylated by the same procedure as in Example 7 to yield 3-(4-acetoxy-3-methoxyphenyl)-2-propenoic acid (p-acetoxy-m-methoxycinnamic acid). The obtained 3-(4-acetoxy-3-methoxyphenyl)-2-propenoic acid (p-acetoxy-m-methoxycinnamic acid) was reacted with SOCl=to prepare p-acetoxy-m-methoxycinnamoyl chloride (3-(4-acetoxy-3-methoxyphenyl)-2-propenoic acid chloride).

The procedure of Example 7 was repeated except that p-acetoxy-m-methoxycinnamoyl chloride (3-(4-acetoxy-3-methoxyphenyl)-2-propenoic acid chloride) rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(4-acetoxy-3-methoxystyryl)carboxyamido-6-amino-3-methyl-1-phenyluracil (yield: 13%).

$^1$H-NMR(CDCl$_3$) δ ppm; 2.32(3H,s; —CO—CH$_3$), 3.39 (3H,s; N—CH$_3$), 3.87(3H,s; —O—CH$_3$), 5.42(2H,brs; —NH$_2$), 6.61(1H,d; —CH=CH—C$_6$H$_3$—), 7.00–7.60(9H,m; N—C$_6$H$_5$+—CH=CH—C$_6$H$_3$—+—CH=CH—C$_6$H$_3$—), 7.79(1H,brs; —NH—CO—)

Mass (m/z): 450(M$^+$)

EXAMPLE 51

6-Amino-3-methyl-5-(4-oxo-4H-pyran-2-yl)carboxyamido-1-phenyluracil

4-Oxo-4H-pyran-2-carboxylic acid was reacted with SOCl$_2$ by the same procedure as in Example 7 to prepare 4-oxo-4H-pyran-2-carbonyl chloride.

The procedure of Example 7 was repeated except that 4-oxo-4H-pyran-2-carbonyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-3-methyl-5-(4-oxo-4H-pyran-2-yl)carboxyamido-1-phenyluracil (yield: 56%).

$^1$H-NMR(CDCl$_3$) δ ppm; 3.24(3H,s; N—CH$_3$), 5.93(2H, brs; —NH$_2$), 6.94(1H,s; 3-position of —CO—C$_5$H$_3$O$_2$), 7.40–7.90(7H,m; N—C$_6$H$_5$+5,6-positions of —CO—C$_5$H$_3$O$_2$), 9.08(1H,brs; —NH—CO—)

Mass (m/z): 354(M$^+$)

EXAMPLE 52

6-Amino-3-methyl-5-(2-oxo-2H-pyran-5-yl)carboxyamido-1-phenyluracil

2-Oxo-2H-pyran-5-carboxylic acid was reacted with SOCl$_2$ by the same procedure as in Example 7 to prepare 2-oxo-2H-pyran-5-carbonyl chloride.

The procedure of Example 7 was repeated except that 2-oxo-2H-pyran-5-carbonyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-3-methyl-5-(2-oxo-2H-pyran-5-yl)carboxyamido-1-phenyluracil (yield: 56%).

$^1$H-NMR(CDCl$_3$) δ ppm; 3.31(3H,s; N—CH$_3$), 5.64(1H, d; 6-position of —CO—C$_5$H$_3$O$_2$), 6.21(2H,brs; —NH$_2$), 7.30–7.80(7H,m; N—C$_6$H$_5$+3,4-positions of —CO—C$_5$H$_3$O$_2$), 10.00(1H,brs; —NH—CO—)

Mass (m/z): 354(M$^+$)

EXAMPLE 53

6-Amino-5-(2-hydroxy-5-methoxyphenyl)carboxyamido-3-methyl-1-phenyluracil

2-Hydroxy-5-methoxybenzoic acid (1.68 g, 11 mM) and pyridine (1.2 ml) were dissolved in 20 ml of chloroform. To the resulting solution was added dropwise 2.1 ml of acetyl chloride slowly at 0° C. Subsequently, the reaction mixture was brought gradually to room temperature and stirred overnight. The solvent was distilled off from the reaction solution under reduced pressure and the residue was dissolved in chloroform and washed with 0.5N hydrochloric acid. Chloroform was then distilled off under reduced pressure to yield acetylated 2-acetoxy-5-methoxybenzoic acid as a white crystal. Subsequently, the white crystal was dissolved in 20 ml of chloroform and 1 ml of SOCl$_2$ was slowly added dropwise. After heating under reflux for 1 hour, the reaction solution was distilled off under reduced pressure to yield 2-acetoxy-5-methoxybenzoyl chloride.

5,6-Diamino-3-methyl-1-phenyluracil (0.7 g, 3 mM) was dissolved in 30 ml of chloroform and 3 ml of pyridine was added. To the resulting solution was added 2-acetoxy-5-methoxybenzoyl chloride (1.3 g, 5 mM) slowly under cooling at 0° C. The reaction mixture was brought gradually to room temperature and heated under reflux for 2 hours. The solvent was distilled off from the reaction solution under reduced pressure and the residue was dissolved in 10 ml of methanol. To the solution was added an aqueous solution of NaHCO$_3$ (3 g/50 ml) for deacetylation and the mixture was stirred for 1 hour. A product was obtained as a white crystal by extraction with chloroform and precipitation from the aqueous layer with hydrocholoric acid. The product gave the following $^1$H-NMR and mass analysis spectra to be identified as the desired compound 6-amino-5-(2-hydroxy-5-methoxyphenyl)carboxyamido-3-methyl-1-phenyluracil (yield: 32%).

$^1$H-NMR(CDCl$_3$) δ ppm; 3.39(3H,s; N—CH$_3$), 3.79(3H, s; —O—CH$_3$), 5.09(2H,brs; —NH$_2$), 6.90–7.60(8H,m; N—C$_6$H$_5$+—C$_6$H$_3$—), 8.30(1H,brs; —NH—CO—), 11.10(1H, brs; —OH)

Mass (m/z): 382 (M$^+$)

EXAMPLE 54

6-Amino-1-(4-fluorophenyl)-5-(2-hydroxy-5-methoxyphenyl)carboxyamido-3-methyluracil The procedure of Example 53 was repeated except that 5,6-diamino-1-(4-fluorophenyl)-3-methyluracil rather than 5,6-diamino-3-methyl-1-phenyluracil was reacted with 2-acetoxy-5-methoxybenzoyl chloride. As a result, a product was obtained as a white crystal. The product gave the following $^1$H-NMR and mass analysis spectra to be identified as the desired compound 6-amino-1-(4-fluorophenyl)-5-(2-hydroxy-5-methoxyphenyl)carboxyamido-3-methyluracil (yield: 45%).

$^1$H-NMR(CDCl$_1$) δ ppm; 3.41(3H,s; N—CH$_3$), 3.82(3H, s; —O—CH$_3$), 5.11(2H,brs; —NH$_2$), 7.00–7.50(7H,m; N—C$_6$H$_4$—+—C$_6$H$_3$—), 8.36(1H,brs; —NH—CO—), 11.12 (1H,brs; —OH)

Mass (m/z): 400(M$^+$)

EXAMPLE 55

5-(2-Acetoxy-5-methoxyphenyl)carboxyamido-6-amino-1-(4-methoxyphenyl)-3-methyluracil The procedure of Example 53 was repeated except that 5,6-diamino-1-(4-methoxyphenyl)-3-methyluracil rather than 5,6-diamino-3-methyl-1-phenyluracil was reacted with 2-acetoxy-5-methoxybenzoyl chloride. In this example, a product was obtained as a pale yellow crystal from a solution obtained just before the deacetylation procedure. The product gave the following $^1$H-NMR and mass analysis spectra to be identified as the desired compound 5-(2-acetoxy-5-methoxyphenyl)carboxyamido-6-amino-1-(4-methoxyphenyl)-3-methyluracil (yield: 41%).

$^1$H-NMR(CDCl$_3$) δ ppm; 2.20(3H,s; —CO—CH$_3$), 3.15 (3H,s; N—CH$_3$), 3.81(3H,s; —O—CH$_3$), 3.83(3H,s; —O—CH$_3$), 5.92(2H,brs; —NH$_2$), 7.00–7.40(7H,m; N—C$_6$H$_4$—+—C$_6$H$_3$—), 8.79(1H,brs; —NH—CO—)

Mass (m/z): 454(M$^+$)

EXAMPLE 56

5-(2-Acetoxyphenyl)carboxyamido-6-amino-3-methyl-1-phenyluracil

The hydroxyl group in 2-hydroxybenzoic acid was acetylated by the same procedure as in Example 7 to yield 2-acetoxybenzoic acid. The obtained 2-acetoxybenzoic acid was reacted with SOCl$_2$ to prepare 2-acetoxybenzoyl chloride.

The procedure of Example 7 was repeated except that 2-acetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(2-acetoxyphenyl)carboxyamido-6-amino-3-methyl-1-phenyluracil (yield: 11%).

$^1$H-NMR(CDCl$_3$) δ ppm; 2.20(3H,s; —CO—CH$_3$), 3.30 (3H,s; N—CH$_3$), 5.31(2H,brs; —NH$_2$), 7.20–7.80(9H,m; N—C$_6$H$_5$+—C$_6$H$_4$—), 8.44(1H,brs; —NH—CO—)

Mass (m/z): 394 (M$^+$)

EXAMPLE 57

5-(3-Acetoxyphenyl)carboxyamido-6-amino-3-methyl-1-phenyluracil

The hydroxyl group in 3-hydroxybenzoic acid was acetylated by the same procedure as in Example 7 to yield 3-acetoxybenzoic acid. The obtained 3-acetoxybenzoic acid was reacted with SOCl$_2$ to prepare 3-acetoxybenzoyl chloride.

The procedure of Example 7 was repeated except that 3-acetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(3-acetoxyphenyl)carboxyamido-6-amino-3-methyl-1-phenyluracil (yield: 12%).

$^1$H-NMR(CDCl$_3$) δ ppm; 2.32(3H,m; —CO—CH$_3$; 3.31 (3H,s; N—CH$_3$), 5.39(2H,brs; —NH$_2$), 7.20–7.90(9H,m; N—C$_6$H$_5$+—C$_6$H$_4$—), 8.69(1H,brs; —NH—CO—)

Mass (m/z): 394 (M$^+$)

EXAMPLE 58

5-(4-Acetoxyphenyl)carboxyamido-6-amino-3-methyl-1-phenyluracil

The hydroxyl group in 4-hydroxybenzoic acid was acetylated by the same procedure as in Example 7 to yield 4-acetoxybenzoic acid. The obtained 4-acetoxybenzoic acid was reacted with SOCl$_2$ to prepare 4-acetoxybenzoyl chloride.

The procedure of Example 7 was repeated except that 4-acetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 5-(4-acetoxyphenyl)carboxyamido-6-amino-3-methyl-1-phenyluracil (yield: 59%).

$^1$H-NMR(CDCl$_3$) δ ppm; 2.28(3H,s; —CO—CH$_3$), 3.33 (3H,s; N—CH$_3$), 5.27(2H,brs; —NH$_2$), 7.10–8.00(9H,m; N—C$_6$H$_5$+—C$_6$H$_4$—), 8.18(1H,brs; —NH—CO—)

Mass (m/z): 394 (M$^+$)

EXAMPLE 59

6-Amino-5-(3,5-diacetoxyphenyl)carboxyamido-3-methyl-1-(1-naphthyl)uracil

N-Methyl-N'-(1-naphthyl)urea was prepared preliminarily from 1-naphthyl isocyanate and methylamine by the same procedure as in Reference Example 1. The urea compound as the starting material was reacted with cyanoacetic acid to form a uracil ring. Using sodium nitrite a nitroso group was introduced into the 5-position of the uracil ring in the obtained 6-amino-3-methyl-1-(1-naphthyl) uracil and then reduced with hydrogen gas to prepare 5,6-diamino-3-methyl-1-(1-naphthyl)uracil.

The procedure of Example 7 was repeated except that 5,6-diamino-3-methyl-1-(1-naphthyl)uracil rather than 5,6-diamino-3-methyl-1-phenyluracil was reacted with 3,5-diacetoxybenzoyl chloride. As a result, a product was obtained as a white crystal. The product gave the following $^1$H-NMR and mass analysis spectra to be identified as the desired compound 6-amino-5-(3,5-diacetoxyphenyl) carboxyamido-3-methyl-1-(1-naphthyl)uracil (yield: 21%).

$^1$H-NMR(CDCl$_3$) δ ppm; 2.30(6H,s; 2×—CO—CH$_3$), 3.36(3H,s; N—CH$_3$), 4.47(2H,brs; —NH$_2$), 7.10–8.05(10H, m; N—C$_{10}$H$_7$+—C$_6$H$_3$—), 7.90(1H,brs; —NH—CO—)

Mass (m/z): 502 (M$^+$)

EXAMPLE 60

6-Amino-3-methyl-5-(4-methylcyclohexyl)carboxyamido-1-phenyluracil

4-Methylcyclohexanecarboxylic acid was reacted with SOCl$_2$ by the same procedure as in Example 7 to prepare 4-methylcyclohexanecarbonyl chloride.

The procedure of Example 7 was repeated except that 4-methylcyclohexylcarbonyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-3-methyl-5-(4-methylcyclohexyl) carboxyamido-1-phenyluracil (yield: 28%).

$^1$H-NMR(CDCl$_3$) δ ppm; 0.90–2.00(13H,m; —C$_6$H$_{10}$—C$_3$), 3.37(3H,s; N—CH$_3$), 5.19(2H,brs; —NH$_2$), 7.30–7.60(5H,m; N—C$_6$H$_5$)

Mass (m/z): 356 (M$^+$)

EXAMPLE 61

6-Amino-3-methyl-5-(1-methylcyclohexyl)carboxyamido-1-phenyluracil

1-Methylcyclohexanecarboxylic acid was reacted with SOCl$_2$ by the same procedure as in Example 7 to prepare 1-methylcyclohexanecarbonyl chloride.

The procedure of Example 7 was repeated except that 1-methylcyclohexanecarbonyl chloride rather than 3,5- diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-3-methyl-5-(1-methylcyclohexyl) carboxyamido-1-phenyluracil (yield: 56%).

$^1$H-NMR(CDCl$_3$) δ ppm; 1.24(3H,m; —C$_6$H$_{10}$—CH$_3$), 1.40–2.10(10H,m; —C$_6$H$_{10}$—CH$_3$), 3.38(3H,s; N—CH$_3$), 5.18(2H,brs; —NH$_2$), 7.20–7.60(5H,m; N—C$_6$H$_5$)

Mass (m/z): 356 (M$^+$)

EXAMPLE 62

6-Amino-5-(2,3-diacetoxyphenyl)carboxyamido-3-methyl-1-phenyluracil

The hydroxyl groups in 2,3-dihydroxybenzoic acid were acetylated by the same procedure as in Example 7 to yield 2,3-diacetoxybenzoic acid. The obtained 2,3-diacetoxybenzoic acid was reacted with SOCl$_2$ to prepare 2,3-diacetoxybenzoyl chloride.

The procedure of Example 7 was repeated except that 2,3-diacetoxybenzoyl chloride rather than 3,5-diacetoxybenzoyl chloride was reacted with 5,6-diamino-3-methyl-1-phenyluracil. As a result, a product was obtained as a white crystal. The product gave the following $^1$H-NMR and mass analysis spectra to be identified as the desired compound 6-amino-5-(2,3-diacetoxyphenyl)carboxyamido-3-methyl-1-phenyluracil (yield: 54%).

$^1$H-NMR(CDCl$_3$) δ ppm; 2.27(3H,s; —CO—CH$_3$ (o-position)), 2.31(3H,s; —CO—CH$_3$ (m-position)), 3.39 (3H,s; N—CH$_3$), 5.30(2H,brs; —NH$_2$), 7.10–7.40(8H,m; N—C$_6$H$_5$+—C$_6$H$_3$—), 8.01(1H,brs; —NH—CO—)

Mass (m/z): 452(M$^+$)

EXAMPLE 63

6-Amino-5-(2,3-diacetoxyphenyl)carboxyamido-1-(4-fluorophenyl)-3-methyluracil

The procedure of Example 62 was repeated except that 5,6-diamino-1-(4-fluorophenyl)-3-methyluracil rather than 5,6-diamino-3-methyl-1-phenyluracil was reacted with 2,3-diacetoxybenzoyl chloride. As a result, a product was obtained as a white crystal. The product gave the following $^1$H-NMR and mass analysis spectra to be identified as the desired compound 6-amino-5-(2,3-diacetoxyphenyl) carboxyamido-1-(4-fluorophenyl)-3-methyluracil (yield: 44%).

$^1$H-NMR(DMSO-d$_6$) δ ppm; 2.30(3H,s; —CO—CH$_3$ (o-position)), 2.36(3H,s; —CO—CH$_3$ (m-position)), 3.15 (3H,s; N—CH$_3$), 6.25(2H,s; —NH$_2$), 7.20–7.60(7H,m; N—C$_6$H$_4$—+—C$_6$H$_3$—), 9.06(1H,brs; —NH—CO—)

Mass (m/z): 470(M$^+$)

EXAMPLE 64

6-Amino-5-(2,3-diacetoxyphenyl)carboxyamido-3-methyl-1-(4-methylphenyl)uracil

The procedure of Example 62 was repeated except that 5,6-diamino-1-(4-methylphenyl)-3-methyluracil rather than 5,6-diamino-3-methyl-1-phenyluracil was reacted with 2,3-diacetoxybenzoyl chloride. As a result, a product was obtained as a white crystal. The product gave the following $^1$H-NMR and mass analysis spectra to be identified as the desired compound 6-amino-5-(2,3-diacetoxyphenyl) carboxyamido-3-methyl-1-(4-methylphenyl)uracil (yield: 38%).

$^1$H-NMR(DMSO-d$_6$) δ ppm; 2.09(3H,s; N—C$_6$H$_4$—CH$_3$), 2.30(3H,s; —CO—CH$_3$ (o-position)), 2.35(3H,s; —CO—CH$_3$ (m-position)), 3.15(3H,s; N—CH$_3$), 6.24(2H,s; —NH$_2$), 7.20–7.70(7H,m; N—C$_6$H$_4$—+—C$_6$H$_3$—), 9.01 (1H,brs; —NH—CO—)

Mass (m/z): 466 (M$^+$)

EXAMPLE 65

6-Amino-5-(2,3-diacetoxyphenyl)carboxyamido-3-methyl-1-(4-methoxyphenyl)uracil

The procedure of Example 62 was repeated except that 5,6-diamino-1-(4-methoxyphenyl)-3-methyluracil rather than 5,6-diamino-3-methyl-1-phenyluracil was reacted with 2,3-diacetoxybenzoyl chloride. As a result, a product was obtained as a white crystal. The product gave the following $^1$H-NMR and mass analysis spectra to be identified as the desired compound 6-amino-5-(2,3-diacetoxyphenyl) carboxyamido-3-methyl-1-(4-methoxyphenyl)uracil (yield: 41%).

$^1$H-NMR(DMSO-d$_6$) δ ppm; 2.30(3H,s; —CO—CH$_3$ (o-position)), 2.36(3H,s; —CO—CH$_3$ (m-position)), 3.14 (3H,s; N—CH$_3$), 3.88(3H,s; —O—CH$_3$), 6.25(2H,s; —NH$_2$), 7.15–7.70(7H,m; N—C$_6$H$_4$—+—C$_6$H$_3$—), 9.04(1H, brs; —NH—CO—)

Mass (m/z): 482(M$^+$)

EXAMPLE 66

5-(3-Acetoxy-5-hydroxyphenyl)carboxyamido-6-amino-3-methyl-1-phenyluracil

6-Amino-5-(3,5-diacetoxyphenyl)carboxyamido-3-methyl-1-phenyluracil (5 g, 11 mM) as prepared in Example 7 was added to 50 ml of ethanol and two drops of aqueous ammonia were added. The resulting solution was heated under reflux for 1 hour and the solvent was then distilled off under reduced pressure. A product was separated and purified from the obtained residue by column chromatography on silica gel [eluent: chloroform/methanol=50/1 (V/V)]. As a result, a white crystalline powder was obtained (0.3 g). The product gave the following $^1$H-NMR and mass analysis spectra to be identified as the desired compound 5-(3-acetoxy-5-hydroxyphenyl)carboxyamido-6-amino-3-methyl-1-phenyluracil (yield: 7%).

$^1$H-NMR(DMSO-d$_6$) δ ppm; 2.27(3H,s; —CO—CH$_3$), 3.15(3H,s; N—CH$_3$), 5.7(1H,s; —OH), 6.03(2H,brs; —NH$_2$), 6.69(1H,m; p-position of —C$_6$H$_3$—), 7.20–7.60(7H, m; N—C$_6$H$_5$+o-position of —C$_6$H$_3$—), 8.89(1H,brs; —NH—CO—)

Mass (m/z): 410(M$^+$)

EXAMPLE 67

6-Amino-3-methyl-1-phenyl-5-(3,4,5-tri-n-butylcarbonyloxyphenyl)carboxyamidouracil 6-Amino-3-methyl-1-phenyl-5-(3,4,5-trihydroxyphenyl) carboxyamidouracil (200 mg, 0.05 mM) as prepared in Example 29 was dissolved in 10 ml of DMF. To the resulting solution were added 0.5 ml of triethylamine and 0.46 g of butyric anhydride (butanoic anhydride) and mixed. The reaction mixture was stirred for 2 hours at room temperature. The solvent was then distilled off from the reaction mixture under reduced pressure and the obtained residue was dissolved in a small amount of ethyl acetate. By crystallization with hexane, a product was obtained as a crystal. The product gave the following $^1$H-NMR and mass analysis spectra to be identified as the desired compound 6-amino-3-methyl-1-phenyl-5-(3,4,5-tri-n-butylcarbonyloxyphenyl) carboxyamidouracil (yield: 278 mg, or 90% based on the compound prepared in Example 29).

$^1$H-NMR(CDCl$_3$) δ ppm: 0.95–1.06(9H,m; 3×—CH$_2$—CH$_2$—CH$_3$), 0.68–0.79(6H,m; 3×—CH$_2$—CH$_2$—CH$_3$), 2.49(6H,t; 3×—CH$_2$—CH$_2$—CH$_3$), 3.34(3H,s; N—CH$_3$), 5.19(2H,s; —NH$_2$), 7.33–7.56(5H,m; N—C$_6$H$_5$), 7.66(2H,s; —C$_6$H$_2$), 8.02(1H,s; —NH—CO—)

Mass (m/z): 594 (M$^+$)

EXAMPLE 68

6-Amino-3-methyl-1-phenyl-5-(3,4,5-triisobutylcarbonyloxyphenyl)carboxyamidouracil 6-Amino-3-methyl-1-phenyl-5-(3,4,5-trihydroxyphenyl) carboxyamidouracil (200 mg, 0.05 mM) as prepared in Example 29 was dissolved in 10 ml of DMF. To the resulting solution were added 0.5 ml of triethylamine and 0.32 g of isobutyric anhydride (2-methylpropanoic anhydride) and mixed. The reaction mixture was stirred for 2 hours at room temperature. The solvent was then distilled off from the reaction mixture under reduced pressure. After addition of water to the residue, a product was obtained as a crystal by sonication. The product gave the following $^1$H-NMR and mass analysis spectra to be identified as the desired compound 6-amino-3-methyl-1-phenyl-5-(3,4,5-triisobutylcarbonyloxyphenyl)carboxyamidouracil (yield: 308 mg, or 100% based on the compound prepared in Example 29).

$^1$H-NMR(CDCl$_3$) δ ppm: 1.30 & 1.31(18H,each s; 3×—CH(—CH$_3$)$_2$), 2.75–2.80(3H,m; 3×—CH(—CH$_3$)$_2$), 3.36(3H,s; N—CH$_3$), 5.19(2H,s; —NH$_2$), 7.36–7.59(5H,m; N—C$_6$H$_5$), 7.67(2H,s; —C$_6$H$_2$), 8.13(1H,s; —NH—CO—)

Mass (m/z): 594 (M$^+$)

EXAMPLE 69

6-Amino-3-methyl-1-phenyl-5-(3,4,5-triethoxycarbonyloxyphenyl)carboxyamidouracil 6-Amino-3-methyl-1-phenyl-5-(3,4,5-trihydroxyphenyl) carboxyamidouracil (195 mg) as prepared in Example 29 was dissolved in 10 ml of DMF. To the resulting solution were added 0.5 ml of triethylamine and 0.25 g of ethyl chloroformate and mixed. The reaction mixture was stirred for 2 hours at room temperature. The solvent was then distilled off from the reaction mixture under reduced pressure. By extraction with dichloromethane-water, a product was extracted from the residue into the dichloromethane layer. The dichloromethane layer was distilled off under reduced pressure and the residue was dissolved in a small amount of ethyl acetate. By crystallization with hexane, a product was obtained as a crystal. The product gave the following $^1$H-NMR and mass analysis spectra to be identified as the desired compound 6-amino-3-methyl-1-phenyl-5-(3,4,5-triethoxycarbonyloxyphenyl)carboxyamidouracil (yield: 290 mg, or 95% based on the compound prepared in Example 29).

$^1$H-NMR(CDCl$_3$) δ ppm: 1.37(9H,t; 3×—CH$_2$—CH$_3$), 3.37(3H,s; N—CH$_3$), 4.28–4.36(6H,q; 3×—CH$_2$—CH$_3$), 5.19(2H,s; —NH$_2$), 7.36–7.59(5H,m; N—C$_6$H$_5$), 7.79(2H,s; —C$_6$H$_2$), 8.03(1H,s; —NH—CO—)

Mass (m/z): 600 (M$^+$)

EXAMPLE 70

6-Amino-3-methyl-1-phenyl-5-(3,4,5-triisobutyloxycarbonyloxyphenyl) carboxyamidouracil 6-Amino-3-methyl-1-phenyl-5-(3,4,5-trihydroxyphenyl) carboxyamidouracil (190 mg) as prepared in Example 29 was dissolved in 10 ml of DMF. To the resulting solution were added 0.5 ml of triethylamine and 0.41 g of isobutyl chloroformate and mixed. The reaction mixture was stirred for 2 hours at room temperature. The solvent was then distilled off from the reaction mixture under reduced pressure. By extraction with dichloromethane-water, a product was extracted from the residue into the dichloromethane layer. The dichloromethane layer was distilled off under reduced pressure and the residue was dissolved in a small amount of ethyl acetate. By crystallization with hexane, a product was obtained as a crystal. The product gave the following $^1$H-NMR and mass analysis spectra to be identified as the desired compound 6-amino-3-methyl-1-phenyl-5-(3,4,5-triisobutyloxycarbonyloxyphenyl) carboxyamidouracil (yield: 289 mg, or 85% based on the compound prepared in Example 29).

$^1$H-NMR(CDCl$_3$) δ ppm: 0.97–1.00(18H,m; 3×—CH$_2$—CH(—CH$_3$)$_2$), 2.02–2.07(3H,s; 3×—CH$_2$—CH(—CH$_3$)$_2$), 3.38(3H,s; N—CH$_3$), 4.04 & 4.06(6H,each s; 3×—CH$_2$—CH(—CH$_3$)$_2$), 5.24(2H,s; —NH$_2$), 7.36–7.60(5H,m; N—C$_6$H$_5$), 7.79(2H,s; —C$_6$H$_2$), 8.00(1H,s; —NH—CO—)

Mass (m/z): 684 (M$^+$)

EXAMPLE 71

Inhibiting effect on a picryl chloride-induced type IV allergy

For the purpose of verifying that the 1-aryluracil derivatives (Ia) of the present invention have an inhibiting effect on type IV allergy, the inhibition of a picryl chloride-induced allergy reaction which is a model of type IV allergy was studied by the following method.

Method

The abdomen of 6-weeks old male ICR strain mice was shaven and 0.1 ml of a 7% picryl chloride solution in acetone was applied to the epithelium of the abdomen for immunization. After one week, 5 μl of a 1% picryl chloride solution in olive oil was applied to both sides of the left auricula to induce an allergy reaction. A given amount of a test substance was suspended in a 0.5% CMC-Na solution and the resulting suspension was administered orally to each mouse twice, i.e., just after the induction and 16 hours after. The thickness of the left auricula was measured both before the induction and 24 hours after.

The difference between the thickness of the left auricula before the induction and the value measured 24 hours after was calculated as the increase in thickness. Using a reference group to which only a 0.5% CMC-Na solution was administered orally, a reference value for the increase in thickness was obtained. The percent inhibition was determined as 100% when the increase in thickness was zero and as 0% when the increase in thickness was equal to the reference value. On the basis of these criteria, the percent inhibition of each test substance was calculated at varying doses. Part of the results obtained in this test are shown in Table 1. In addition, the result of the administration of prednisolone as a positive control compound is shown in Table 1.

The results shown in Table 1 reveal that the 1-aryluracil derivatives (Ia) of the present invention have an inhibiting effect on a picryl chloride-induced allergy reaction. Furthermore, it can be found that their effect is comparable to that of the positive control compound, prednisolone, at the same dose. Consequently, it is clear that the 1-aryluracil derivatives (Ia) of the present invention exhibit comparable drug efficacy to prednisolone as a therapeutic agent of type IV allergy.

TABLE 1

| Test Substance | Dose (mg/kg) | Percent Inhibition (%) |
| --- | --- | --- |
| Compound Prepared in Example 1 | 10 | 54 |
| Compound Prepared in Example 2 | 3 | 38 |
| Compound Prepared in Example 3 | 10 | 33 |
| Compound Prepared in Example 4 | 10 | 35 |
| Compound Prepared in Example 7 | 10 | 65 |
| Compound Prepared in Example 8 | 10 | 43 |
| Compound Prepared in Example 11 | 100 | 30 |
| Compound Prepared in Example 14 | 10 | 45 |
| Compound Prepared in Example 22 | 100 | 72 |
|  | 10 | 48 |
| Compound Prepared in Example 34 | 100 | 52 |
|  | 10 | 33 |
| Compound Prepared in Example 51 | 10 | 45 |
| Compound Prepared in Example 52 | 100 | 39 |
|  | 10 | 19 |
| Compound Prepared in Example 53 | 10 | 45 |
| Compound Prepared in Example 55 | 100 | 35 |
| Compound Prepared in Example 60 | 10 | 40 |
| Compound Prepared in Example 61 | 100 | 32 |
| (Positive Control Compound) Prednisolone | 10 | 77 |

EXAMPLE 72

Inhibiting effect on a 48 hour PCA reaction

For the purpose of verifying that the 1-aryluracil derivatives (Ia) of the present invention have an inhibiting effect on type I allergy, the inhibition of a passive cutaneous anaphylaxis (PCA) reaction which is a model of type I allergy was studied by the following method.

(Test method for compound prepared in Example 22)

Eight-weeks old male Wistar strain rats were immunized by subcutaneously injecting 0.1 ml of 700-fold diluted DNP-Ascaris antiserum (titer=1:1024) at two positions on the dorsum. Forty-eight hours after the immunization, 1 ml of a 0.5% Evans blue solution containing 1 mg of DNP-Ascaris antigen was administered into a pedal vein to induce a PCA reaction. Thirty minutes after the induction, the rats were bled to death and blue circular parts appearing at the immunized positions were excised. The dye was extracted from the blue circular parts with ethyl acetate and the amount of the dye leakage was determined. A test substance was suspended in a 0.5% CMC-Na solution and administered orally to each rat at a dose of 100 mg/kg 30 minutes before the induction.

Using a reference group to which only a 0.5% CMC-Na solution was administered orally, a reference value for the amount of dye leakage was obtained. The percent inhibition was determined as 100% when the amount of dye leakage was zero and as 0% when the amount of dye leakage was equal to the reference value. On the basis of these criteria, the percent inhibition of each test substance was calculated at varying doses. Part of the results obtained in this test are shown in Table 2. In addition, the result of the administration of tranilast as a positive control compound is shown in Table 2.

The results shown in Table 2 reveal that the 1-aryluracil derivatives (Ia) of the present invention have an inhibiting effect on a PCA reaction. Furthermore, it can be found that their effect is comparable to that of the positive control compound, tranilast, at the same dose. Consequently, it is clear that the 1-aryluracil derivatives (Ia) of the present invention exhibit comparable drug efficacy to tranilast as a therapeutic agent of type I allergy.

TABLE 2

| Test Substance | Percent Inhibition (%) |
| --- | --- |
| Compound Prepared in Example 22 | 50 |
| (Positive Control Compound) Tranilast | 35 |

(Test method for compound prepared in Example 1)

Eight-weeks old male Wistar strain rats were immunized by subcutaneously injecting 0.05 ml of 50-fold diluted DNP-Ascaris antiserum (titer=1:64) at four positions on the dorsum. Forty-eight hours after the immunization, 1 ml of a 0.5% Evans blue solution containing 1 mg of DNP-Ascaris antigen was administered into a tail vein to induce a PCA reaction. Thirty minutes after the induction, the rats were bled to death and blue circular parts appearing at the immunized positions were excised. The dye was extracted from the blue circular parts with ethyl acetate and the amount of the dye leakage was determined. A test substance was suspended in a 0.5% CMC-Na solution and administered orally to each rat 1 hour before the induction.

Using a reference group to which only a 0.5% CMC-Na solution was administered orally, a reference value for the amount of dye leakage was obtained. The percent inhibition was determined as 100% when the amount of dye leakage was zero and as 0% when the amount of dye leakage was equal to the reference value. On the basis of these criteria, the percent inhibition of each test substance was calculated at varying doses. Part of the results obtained in this test are shown in Table 3. In addition, the result of the administration of tranilast as a positive control compound is shown in Table 3.

The results shown in Table 3 reveal that the 1-aryluracil derivatives (Ia) of the present invention have an inhibiting effect on a PCA reaction. Furthermore, it can be found that their effect is comparable to that of the positive control compound, tranilast. Consequently, it is clear that the 1-aryluracil derivatives (Ia) of the present invention exhibit comparable drug efficacy to tranilast as a therapeutic agent of type I allergy.

TABLE 3

| Test Substance | Dose (mg/kg) | Percent Inhibition (%) |
| --- | --- | --- |
| Compound Prepared in Example 1 | 3 | 33 |
|  | 30 | 49 |
| (Positive Control Compound) Tranilast | 100 | 66 |

The results of the test for verifying the inhibiting effect on a picryl chloride-induced allergy reaction which is a model of type IV allergy and those of the test for verifying the inhibiting effect on a PCA reaction which is a model of type I allergy reveal that the 1-aryluracil derivatives (Ia) of the present invention can be used as therapeutic agents of a wide variety of allergic diseases classified as allergies of types I and IV, particularly type I allergy characterized by great contribution from type IV allergy and a mixed allergy of types I and IV. Specifically, the 1-aryluracil derivatives (Ia) of the present invention are useful as therapeutic agents for inhibiting or alleviating asthma, allergic diseases that have manifestations of inflammations such as dermatitis or rhinitis, for example, atopic dermatitis, symptoms such as bronchoconstriction accompanied by asthma, and allergic diseases such as graft-versus-host disease (GVHD) that develops after organ transplantion.

Experimental Example 1

Toxicity Test

The 1-aryluracil derivatives (Ia) of the present invention were tested for toxicity by the following method.

A test substance was suspended in a 0.5% CMC-Na solution and administered orally to 6-weeks old male SD rats once a day at a dose of 1,000 mg/kg for 2 consecutive weeks. The weight of each rat was measured both before the administration and every day during the administration. A given amount of blood was collected on the day after the end of the administration period and examined. Collected urine was also examined. In addition, organs were checked for any aberrations by autopsy.

In the cases where the compounds prepared in Examples 7 and 53 were respectively administered, no rat died during the administration period and no abnormality was observed in the weight change, blood and urine examinations and autopsy. These results suggest very low toxicity of these compounds.

EXAMPLE 73

Formulation Example

Tablets containing the compound prepared in Example 22 as an active ingredient were prepared according to the following formulation.

| (Formulation) | |
|---|---|
| Compound Prepared in Example 22 | 100 mg |
| Magnesium stearate | 30 mg |
| Hydroxypropylmethyl cellulose | 2 mg |
| Polyethylene glycol 6000 | 0.5 mg |
| Lactose | balance |
| Total weight per tablet | 200 mg |

EXAMPLE 74

8-(3,5-Di-tert-butyl-4-hydroxyphenyl)-1-methyl-3-phenylpurine-2,6-dione 5,6-Diamino-3-methyl-1-phenyluracil (0.232 g, 1 mM) as prepared in Reference Example 1, 4-hydroxy-3,5-di-tert-butylbenzaldehyde (0.257 g, 1.1 mM) and p-tosyl acid (p-toluenesulfonic acid, 5 mg) were added to 20 ml of ethanol and the resulting solution was heated under reflux for 4 hours. The solvent ethanol was distilled off under reduced pressure. Thionyl chloride (2 ml) was added to the residue and the mixture was heated under reflux for an additional 10 minutes. The solvent was distilled off under reduced pressure and aqueous ammonia was then added, followed by stirring overnight (approximately 14 hours). A product was then obtained as a pale yellow crystal by crystallization with 20 ml of ethanol and recovered by filtration.

The compound as the pale yellow crystal gave the following $^1$H-NMR and mass analysis spectra to be identified as 8-(3,5-di-tert-butyl-4-hydroxyphenyl)-1-methyl-3-phenylpurine-2,6-dione.(yield: 0.25 g, or 56% based on 5,6-diamino-3-methyl-1-phenyluracil).

$^1$H-NMR(CDCl$_3$) δ ppm; 1.43(18H,s, t-Bu×2), 3.50(3H,s, N—CH$_3$), 5.53(1H,s, OH), 7.40–7.70(7H,m, —C$_6$H$_2$—+ N—C$_6$H$_5$), 10.60(1H,brs, NH)

Mass (m/z): 446(M$^+$)

EXAMPLE 75

8-(3,5-Di-tert-butyl-4-hydroxyphenyl)-3-(4-methoxyphenyl)-1-methylpurine-2,6-dione 5,6-Diamino-1-(4-methoxyphenyl)-3-methyluracil was prepared by the same procedure as in Reference Example 1. The procedure of Example 74 was repeated except that this 5,6-diamino-1-(4-methoxyphenyl)-3-methyluracil rather than 5,6-diamino-3-methyl-1-phenyluracil was reacted with 4-hydroxy-3,5-di-tert-butylbenzaldehyde. A product was then obtained as a pale yellow crystal by crystallization with ethanol and recovered by filtration.

The compound as the pale yellow crystal gave the following $^1$H-NMR and mass analysis spectra to be identified as 8-(3,5-di-tert-butyl-4-hydroxyphenyl)-3-(4-methoxyphenyl)-1-methylpurine-2,6-dione (yield: 59% based on 5,6-diamino-1-(4-methoxyphenyl)-3-methyluracil).

$^1$H-NMR(CDCl$_3$) δ ppm; 1.38(18H,s, t-Bu×2), 3.30(3H,s, N—CH$_3$), 3.84(3H,s, O—CH$_3$), 7.23(4H,dd, N—C$_6$H$_4$—), 7.82(2H,d, —C$_6$H$_2$—), 9.64(1H,brs, NH)

Mass (m/z): 476 (M$^+$)

EXAMPLE 76

8-(3,5-Di-tert-butyl-4-hydroxyphenyl)-1-methyl-3-(4-methylphenyl)purine-2,6-dione 5,6-Diamino-1-(4-methylphenyl)-3-methyluracil was prepared by the same procedure as in Reference Example 1. The procedure of Example 74 was repeated except that this 5,6-diamino-1-(4-methylphenyl)-3-methyluracil rather than 5,6-diamino-3-methyl-1-phenyluracil was reacted with 4-hydroxy-3,5-di-tert-butylbenzaldehyde. A product was then obtained as a pale yellow crystal by crystallization with ethanol and recovered by filtration.

The compound as the pale yellow crystal gave the following $^1$H-NMR and mass analysis spectra to be identified as 8-(3,5-di-tert-butyl-4-hydroxyphenyl)-1-methyl-3-(4-methylphenyl)purine-2,6-dione (yield: 49% based on 5,6-diamino-1-(4-methylphenyl)-3-methyluracil).

$^1$H-NMR(CDCl$_3$) δ ppm; 1.40(18H,s, t-Bu×2), 2.39(3H,s, N—C$_6$H$_4$—CH$_3$), 3.31(3H,s, N—CH$_3$), 7.31(4H,dd, N—C$_6$H$_4$—), 7.80(2H,s, —C$_6$H$_2$—), 9.54(1H,brs, NH)

Mass (m/z): 460 (M$^+$)

EXAMPLE 77

8-(3,5-Di-tert-butyl-4-hydroxyphenyl)-3-(4-fluorophenyl)-1-methylpurine-2,6-dione 5,6-Diamino-1-(4-fluorophenyl)-3-methyluracil was prepared by the same procedure as in Reference Example 1. The procedure of Example 74 was repeated except that this 5,6-diamino-1-(4-fluorophenyl)-3-methyluracil rather than 5,6-diamino-3-methyl-1-phenyluracil was reacted with 4-hydroxy-3,5-di-tert-butylbenzaldehyde. A product was then obtained as a pale yellow crystal by crystallization with ethanol and recovered by filtration.

The compound as the pale yellow crystal gave the following $^1$H-NMR and mass analysis spectra to be identified as 8-(3,5-di-tert-butyl-4-hydroxyphenyl)-3-(4-fluorophenyl)-1-methylpurine-2,6-dione (yield: 46% based on 5,6-diamino-1-(4-fluorophenyl)-3-methyluracil).

$^1$H-NMR(CDCl$_3$) δ ppm; 1.47(18H,s, t-Bu×2), 3.39(3H,s, N—CH$_3$), 7.40(4H,dd, N—C$_6$H$_4$—), 7.90(2H,s, —C$_6$H$_2$—), 9.55(1H,brs, NH)

Mass (m/z): 464(M$^+$)

EXAMPLE 78

8-(3,4-Dihydroxyphenyl)-1-methyl-3-phenylpurine-2,6-dione

The procedure of Example 74 was repeated except that 3,4-dihydroxybenzaldehyde rather than 4-hydroxy-3,5-di-tert-butylbenzaldehyde was reacted with 5,6-diamino-3-methyl-1-phenyluracil. A product was then obtained as a pale yellow crystal by crystallization with ethanol and recovered by filtration.

The compound as the pale yellow crystal gave the following $^1$H-NMR and mass analysis spectra to be identified as 8-(3,4-dihydroxyphenyl)-1-methyl-3-phenylpurine-2,6-dione (yield: 48% based on 5,6-diamino-3-methyl-1-phenyluracil).

$^1$H-NMR(CDCl$_3$) δ ppm; 3.31(3H,s, N—CH$_3$), 6.78–7.60 (8H,m, N—C$_6$H$_5$+—C$_6$H$_3$—), 9.34(1H,brs, NH)

Mass (m/z): 350(M$^+$)

EXAMPLE 79

8-(3,5-Dihydroxyphenyl)-1-methyl-3-phenylpurine-2,6-dione

The procedure of Example 74 was repeated except that 3,5-dihydroxybenzaldehyde rather than 4-hydroxy-3,5-di-tert-butylbenzaldehyde was reacted with 5,6-diamino-3-methyl-1-phenyluracil. A product was then obtained as a white crystal by crystallization with ethanol and recovered by filtration.

The compound as the white crystal gave the following $^1$H-NMR and mass analysis spectra to be identified as 8-(3,5-dihydroxyphenyl)-1-methyl-3-phenylpurine-2,6-dione (yield: 52% based on 5,6-diamino-3-methyl-1-phenyluracil).

$^1$H-NMR(CDCl$_3$) δ ppm; 3.37(3H,s, N—CH$_3$), 6.90–7.70 (8H,m, N—C$_6$H$_5$+—C$_6$H$_3$—), 9.15(1H,brs, NH)

Mass (m/z): 350(M$^+$)

EXAMPLE 80

1-Methyl-3-phenyl-8-(3,4,5-triacetoxyphenyl)purine-2,6-dione

The procedure of Example 74 was repeated except that 3,4,5-triacetoxybenzaldehyde rather than 4-hydroxy-3,5-di-tert-butylbenzaldehyde was reacted with 5,6-diamino-3-methyl-1-phenyluracil under a stream of argon. A product was then obtained as a white crystal by crystallization with ethanol and recovered by filtration.

The compound as the white crystal gave the following $^1$H-NMR and mass analysis spectra to be identified as 1-methyl-3-phenyl-8-(3,4,5-triacetoxyphenyl)purine-2,6-dione (yield: 41% based on 5,6-diamino-3-methyl-1-phenyluracil).

$^1$H-NMR(CDCl$_3$) δ ppm; 2.29(9H,s, —CO—CH$_3$×3), 3.37(3H,s, N—CH$_3$), 7.40–7.90(7H,m, N—C$_6$H$_5$+—C$_6$H$_2$—), 14.00(1H,brs, NH)

Mass (m/z): 492(M$^+$)

EXAMPLE 81

8-(3,5-Diacetoxyphenyl)-1-methyl-3-phenylpurine-2,6-dione

The procedure of Example 74 was repeated except that 3,5-diacetoxybenzaldehyde rather than 4-hydroxy-3,5-di-tert-butylbenzaldehyde was reacted with 5,6-diamino-3-methyl-1-phenyluracil. A product was then obtained as a white crystal by crystallization with ethanol and recovered by filtration.

The compound as the white crystal gave the following $^1$H-NMR and mass analysis spectra to be identified as 8-(3,5-diacetoxyphenyl)-1-methyl-3-phenylpurine-2,6-dione (yield: 57% based on 5,6-diamino-3-methyl-1-phenyluracil).

$^1$H-NMR(CDCl$_3$) δ ppm; 2.27(3H,s, —CO—CH$_3$), 2.33 (3H,s, —CO—CH$_3$), 3.348(3H,s, N—CH$_3$), 7.10–7.50(8H, m, N—C$_6$H$_5$+—C$_6$H$_3$—), 8.31(1H,brs, NH)

Mass (m/z): 434(M$^+$)

EXAMPLE 82

1-Methyl-3-phenyl-8-(3,4,5-trihydroxyphenyl)purine-2,6-dione

The procedure of Example 74 was repeated except that 3,4,5-trihydroxybenzaldehyde rather than 4-hydroxy-3,5-di-tert-butylbenzaldehyde was reacted with 5,6-diamino-3-methyl-1-phenyluracil under a stream of argon. A product was then obtained as a white crystal by crystallization with ethanol and recovered by filtration.

The compound as the white crystal gave the following $^1$H-NMR and mass analysis spectra to be identified as 1-methyl-3-phenyl-8-(3,4,5-trihydroxyphenyl)purine-2,6-dione (yield: 27% based on 5,6-diamino-3-methyl-1-phenyluracil).

$^1$H-NMR(CDCl$_3$) δ ppm; 3.31(3H,s, N—CH$_3$), 7.00–7.60 (7H,m, N—C$_6$H$_5$+—C$_6$H$_2$—), 9.21(1H,brs, NH)

Mass (m/z): 366(M$^+$)

EXAMPLE 83

Inhibiting effect on a picryl chloride-induced type IV allergy

For the purpose of verifying that the 3-arylpurine derivatives (Ib) of the present invention have an inhibiting effect on type IV allergy, the inhibition of a picryl chloride-induced allergy reaction which is a model of type IV allergy was studied by the following method.

Method

The abdomen of 6-weeks old male ICR strain mice was shaven and 0.1 ml of a 7% picryl chloride solution in acetone was applied to the epithelium of the abdomen for immunization. After one week, 5 μl of a 1% picryl chloride solution in olive oil was applied to both sides of the left auricula to induce an allergy reaction. A given amount of a test substance was suspended in a 0.5% CMC-Na solution and the resulting suspension was administered orally to each mouse twice, i.e., just after the induction and 16 hours after. The thickness of the left auricula was measured both before the induction and 24 hours after.

The difference between the thickness of the left auricula before the induction and the value measured 24 hours after was calculated as the increase in thickness. Using a reference group to which only a 0.5% CMC-Na solution was administered orally, a reference value for the increase in thickness was obtained. The percent inhibition was determined as 100% when the increase in thickness was zero and as 0% when the increase in thickness was equal to the reference value. On the basis of these criteria, the percent inhibition of each test substance was calculated at varying doses. Part of the results obtained in this test are shown in Table 3. In addition, the result of the administration of asteroid agent, prednisolone, as a positive control compound is shown in Table 4.

The results shown in Table 4 reveal that the 3-arylpurine derivatives (Ib) of the present invention have an inhibiting effect on a picryl chloride-induced allergy reaction. Furthermore, it can be found that their effect is comparable to that of the positive control compound, prednisolone, at the same dose. Consequently, it is clear that the 3-arylpUrine derivatives (Ib) of the present invention exhibit comparable drug efficacy to the steroid agent, prednisolone, as a therapeutic agent of type IV allergy.

TABLE 4

| Test Substance | Dose (mg/kg) | Percent Inhibition (%) |
|---|---|---|
| Compound Prepared in Example 74 | 10 | 38 |
| Compound Prepared in Example 75 | 10 | 16 |
|  | 100 | 34 |
| Compound Prepared in Example 78 | 10 | 35 |
| Compound Prepared in Example 80 | 10 | 37 |
|  | 100 | 53 |
| (Positive Control Compound) Prednisolone | 10 | 67 |

Experimental Example 2

Toxicity Test

The 3-arylpurine derivatives (Ib) of the present invention were tested for toxicity by the following method.

A test substance was suspended in a 0.5% CMC-Na solution and administered orally to 6-weeks old male SD rats once a day at a dose of 1,000 mg/kg for 2 consecutive weeks. The weight of each rat was measured both before the administration and every day during the administration. A given amount of blood was collected on the day after the end of the administration period and examined. Collected urine was also examined. In addition, organs were checked for any aberrations by autopsy.

In the case where the compound prepared in Example 74 was administered, no rat died during the administration period and no abnormality was observed in the weight change, blood and urine examinations and autopsy. These results suggest very low toxicity of the 3-arylpurine derivatives (Ib) of the present invention.

EXAMPLE 84

Formulation Example

Tablets containing the compound prepared in Example 80 as an active ingredient were prepared according to the following formulation.

| (Formulation) | |
|---|---|
| Compound Prepared in Example 80 | 100 mg |
| Magnesium stearate | 30 mg |
| Hydroxypropylmethyl cellulose | 2 mg |
| Polyethylene glycol 6000 | 0.5 mg |
| Lactose | balance |
| Total weight per tablet | 200 mg |

What is claimed is:

1. A 3-arylpurine derivative represented by general formula (Ib):

(Ib)

wherein $R_1$ is H, $C_{1-6}$ alkyl or aralkyl;

Ar is 1-naphthyl or a group represented by general formula (II):

(II)

wherein $R_2$ is H, halogen, $C_{1-4}$ alkyl or $C_{1-4}$ alkoxy;

$R_4$ is a group represented by general formula (III):

(III)

wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, a group represented by general formula (IV):

(IV)

wherein $R_{21}$, $R_{22}$, $R_{23}$, $R_{24}$ and $R_{25}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, 1-methylcyclohexyl, 4-methylcyclohexyl, 4-oxo-4H-pyran-2-yl or 2-oxo-2H-pyran-5-yl; and $R_6$ is H or $C_{1-4}$ alkyl, or a pharmaceutically acceptable salt thereof.

2. A 1-arylpyrimidine derivative of general formula (Ia):

(Ia)

wherein $R_1$ is H, $C_{1-6}$ alkyl or aralkyl;

Ar is 1-naphthyl or a group represented by general formula (II):

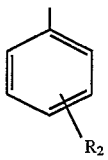

wherein $R_2$ is H, halogen, $C_{1-4}$ alkyl or $C_{1-4}$ alkoxy;
$R_4$ is a group represented by general formula (III):

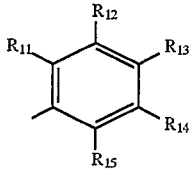

wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, a group represented by general formula (IV):

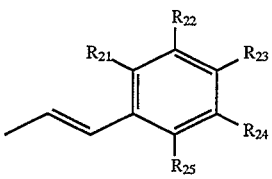

wherein $R_{21}$, $R_{22}$, $R_{23}$, $R_{24}$ and $R_{25}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least one of them is not H, 1-methylcyclohexyl, 4-methylcyclohexyl, 4-oxo-4H-pyran-2-yl or 2-oxo-2H-pyran-5-yl; and $R_5$ and $R_6$ are each independently H or $C_{1-4}$ alkyl,
or a pharmaceutically acceptable salt thereof.

3. The compound of claim 2, wherein $R_5$ or $R_6$ in the general formula (Ia) is H.

4. The compound of claim 2, wherein $R_4$ in the general formula (Ia) is a group represented by the general formula (III).

5. The compound of claim 2, wherein Ar in the general formula (Ia) is a group represented by the general formula (II).

6. The compound of claim 2, wherein $R_4$ in the general formula (Ia) is a group represented by the general formula (IV).

7. The compound of claim 2, wherein $R_4$ in the general formula (Ia) is 1-methylcyclohexyl, 4-methylcyclohexyl, 4-oxo-4H-pyran-2-yl, or 2-oxo-2H-pyran-5-yl.

8. The compound of claim 2, wherein Ar in the general formula (Ia) is 1-naphthyl.

9. The compound of claim 2, wherein $R_4$ in the general formula (Ia) is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

10. The compound of claim 6, wherein $R_4$ in the general formula (Ia) is a group represented by the general formula (IV) wherein $R_{21}$, $R_{22}$, $R_{23}$, $R_{24}$ and $R_{25}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

11. The compound of claim 3, wherein Ar in the general formula (Ia) is 1-naphthyl and $R_4$ is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

12. The compound of claim 5, wherein Ar in the general formula (Ia) is a group represented by the general formula (II) wherein $R_2$ is a substituent at the p-position.

13. The compound of claim 3, wherein $R_4$ in the general formula (Ia) is a group represented by the general formula (III) wherein $R_{12}$, $R_{13}$ and $R_{14}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{11}$ and $R_{15}$ are H.

14. The compound of claim 10, wherein $R_4$ in the general formula (Ia) is a group represented by the general formula (IV) wherein $R_{22}$, $R_{23}$ and $R_{24}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{21}$ and $R_{25}$ are H.

15. The compound of claim 13, wherein $R_4$ in the general formula (Ia) is a group represented by the general formula (III) wherein $R_{12}$, $R_{13}$ and $R_{14}$ are each independently H, OH, $C_{2-10}$ alkanoyloxy or $C_{2-10}$ alkoxycarbonyloxy, provided that at least two of them are not H, and both $R_{11}$ and $R_{15}$ are H.

16. The compound of claim 15, wherein $R_4$ in the general formula (Ia) is 3,5-diacetoxyphenyl, 3,5-dihydroxyphenyl, 3,4,5-triacetoxyphenyl, 3,4,5-trihydroxyphenyl, 3,4-diacetoxyphenyl or 3,4-dihydroxyphenyl.

17. The compound of claim 1, wherein $R_1$ and $R_6$ are as defined above, Ar is a group represented by the general formula (II) and $R_4$ is a group represented by the general formula (III).

18. The compound of claim 17, wherein $R_6$ in the general formula (Ib) is H.

19. The compound of claim 18, wherein Ar in the general formula (Ib) is a group represented by the general formula (II) wherein $R_2$ is a substituent at the p-position.

20. The compound of claim 18, wherein $R_4$ in the general formula (Ib) is a group represented by the general formula (III) wherein $R_{11}$, $R_{12}$, $R_{13}$, $R_{14}$ and $R_{15}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H.

21. The compound of claim 20, wherein $R_4$ in the general formula (Ib) is a group represented by the general formula (III) wherein $R_{12}$, $R_{13}$ and $R_{14}$ are each independently H, OH, $C_{2-10}$ alkanoyloxy, $C_{2-10}$ alkoxycarbonyloxy, $C_{1-4}$ alkyl or $C_{1-4}$ alkoxy, provided that at least two of them are not H, and both $R_{11}$ and $R_{15}$ are H.

22. The compound of claim 21, wherein $R_4$ in the general formula (Ib) is a group represented by the general formula (III) wherein $R_{12}$, $R_{13}$ and $R_{14}$ are each independently H, OH, $C_{2-10}$ alkanoyloxy or $C_{2-10}$ alkoxycarbonyloxy, provided that at least two of them are not H, and both $R_{11}$ and $R_{15}$ are H.

23. The compound of claim 22, wherein $R_4$ in the general formula (Ib) is 3,5-diacetoxyphenyl, 3,5-dihydroxyphenyl, 3,4,5-triacetoxyphenyl, 3,4,5-trihydroxyphenyl, 3,4-diacetoxyphenyl or 3,4-dihydroxyphenyl.

24. A method for treating asthma-accompanied bronchoconstriction comprising administering an amount of a compound of claim 1 effective to treat asthma-accompanied bronchoconstriction to a patient in need thereof.

25. A method for treating atopic dermatitis comprising administering an amount of a compound of claim 1 effective to treat atopic dermatitis to a patient in need thereof.

26. A method for treating an allergic disorder comprising administering an amount of a compound of claim 1 effective to treat an allergic disorder to a patient in need thereof.

27. A method for treating graft-versus-host disease comprising administering an amount of a compound of claim 1 effective to treat graft-versus-host disease to a patient in need thereof.

28. A method for treating asthma-accompanied bronchoconstriction comprising administering an amount of a compound of claim 2 effective to treat asthma-accompanied bronchoconstriction to a patient in need thereof.

29. A method for treating atopic dermatitis comprising administering an amount of a compound of claim 2 effective to treat atopic dermatitis to a patient in need thereof.

30. A method for treating an allergic disorder comprising administering an amount of a compound of claim 2 effective to treat an allergic disorder to a patient in need thereof.

31. A method for treating graft-versus-host disease comprising administering an amount of a compound of claim 2 effective to treat graft-versus-host disease to a patient in need thereof.

* * * * *